(12) United States Patent
Ushida et al.

(10) Patent No.: US 7,829,679 B2
(45) Date of Patent: Nov. 9, 2010

(54) MUCIN-TYPE GLYCOPROTEIN AND USE THEREOF

(75) Inventors: Kiminori Ushida, Saitama (JP); Akiko Masuda, Saitama (JP); Naoshi Dohmae, Saitama (JP); Hidemitsu Furukawa, Saitama (JP); Atsushi Miyawaki, Saitama (JP)

(73) Assignee: Riken, Wako-shi (JP)

( * ) Notice: Subject to any disclaimer, the term of this patent is extended or adjusted under 35 U.S.C. 154(b) by 444 days.

(21) Appl. No.: 12/063,498

(22) PCT Filed: Aug. 11, 2006

(86) PCT No.: PCT/JP2006/315939

§ 371 (c)(1), (2), (4) Date: Feb. 11, 2008

(87) PCT Pub. No.: WO2007/020889

PCT Pub. Date: Feb. 22, 2007

(65) Prior Publication Data

US 2010/0151514 A1 Jun. 17, 2010

(30) Foreign Application Priority Data

Aug. 12, 2005 (JP) .............................. 2005-234108

(51) Int. Cl.
C07K 17/00 (2006.01)
C08H 1/00 (2006.01)
A61K 38/16 (2006.01)

(52) U.S. Cl. ............................. 530/395; 530/402; 514/8
(58) Field of Classification Search ........................ None
See application file for complete search history.

(56) References Cited

FOREIGN PATENT DOCUMENTS

| JP | 5-310799 | 11/1993 |
|---|---|---|
| JP | 6-199900 | 7/1994 |
| JP | 6-217737 | 8/1994 |
| JP | 7-33623 | 2/1995 |
| JP | 7-126292 | 5/1995 |
| JP | WO 95/17428 | 6/1995 |
| JP | 8-256788 | 10/1996 |
| JP | 8-269091 | 10/1996 |
| JP | 10-60005 | 3/1998 |
| JP | 2001-178492 | 7/2001 |
| JP | 2002-143824 | 5/2002 |
| JP | 2002-370991 | 12/2002 |
| JP | 2003-321497 | 11/2003 |
| JP | 2004-99513 | 4/2004 |
| WO | WO 96/13516 | 5/1996 |
| WO | WO 99/63964 | 12/1999 |

OTHER PUBLICATIONS

Veronique Guyonnet Duperat, et al., "Characterization of the Human Mucin Gene MUC5AC: A Consensus Cysteine-Rich Domain for 11p15 Mucin Genes?", Biochem. J., vol. 305, pp. 211-219, 1995.
Joseph A. Bedell, et al., "Sorghum Genome Sequencing by Methylation Filtration", Plos Biology, vol. 3, No. 1, e13, pp. 103-115, 2005.
Toshio Ota, et al., "Complete Sequencing and Characterization of 21,243 Full-Length Human cDNAs", Nature Genetics, vol. 36, No. 1, pp. 40-44, 2004.
Randolph B Caldwell, et al., "Full-Length cDNAs From Chicken Bursal Lymphocytes to Facilitate Gene Function Analysis", Genome Biology vol. 6, No. 1, Article R6, 2004.
Hugh W. Ducklow, et al., "Composition of Mucus Released by Coral Reef Coelenterates", Limnology and Oceanography, vol. 24, No. 4, XP-002513892, 1979, pp. 706-714.
Susanne Reber-Müller, et al., "An Extracellular Matrix Protein of Jellyfish Homologous to Mammalian Fibrillins Forms Different Fibrils Depending on the Life Stage of the Animal", Developmental Biology, vol. 169, No. 2, XP-002117293, Jun. 1, 1995, pp. 662-672.
P.W.M. Reisinger, et al., "Glykoproteinstrukturen in der Mesogloea der Meduse *Aurelia aurita*", Anatomical Gazette: Central Organ for all Scientists, XP-009111631, 1990, pp. 131-132.
Mary N. Arai, et al., "Biochemical Composition of Fed and Starved *Aequorea victoria*", Journal of Experimental Marine Biology and Ecology, vol. 127, No. 3, XP-002513893, 1989, pp. 289-299.
Akiko Masuda, et al., "Mucin (Qniumucin), a Glycoprotein From Jellyfish, and Determination of Its Main Chain Structure", Journal of Natural Products, vol. 70, No. 7, XP-002513894, Jul. 2007, pp. 1089-1092.

*Primary Examiner*—David J Steadman
*Assistant Examiner*—Alexander D Kim
(74) *Attorney, Agent, or Firm*—Oblon, Spivak, McClelland, Maier & Neustadt, L.L.P.

(57) ABSTRACT

Provided is a novel mucin-type glycoprotein and a method for producing the same. Specifically, a mucin-type glycoprotein having a repeat structure including 3 to 2000 repeating units each having an amino acid sequence represented by the formula I: Val-Xaa-Glu-Thr-Thr-Ala-Ala-Pro [wherein Xaa represents Val or Ile] (SEQ ID NO: 1), wherein one or more amino acid residues in the structure are bound to a sugar chain of one or more monosaccharides. Also provided is a composition containing the novel mucin-type glycoprotein. Further provided is a molecular weight marker containing the novel mucin-type glycoprotein.

17 Claims, 15 Drawing Sheets

Fig. 4

| Composition analysis of amino acids of Aurelia aurita | | | | Composition analysis of amino acids of Chrysaora melanaster | | | |
|---|---|---|---|---|---|---|---|
| R.T. | Concentration (nmol) | Peak | Concentration ratio | R.T. | Concentration (nmol) | Peak | Concentration ratio |
| 11.62 | 0.11 | Asp | | 11.59 | 0.03 | Asp | |
| 14.23 | 2.33 | Thr | 2 | 14.327 | 0.78 | Thr | 2 |
| 15.33 | 0.06 | Ser | | 15.473 | 0.05 | Ser | |
| 18.44 | 1.30 | Glu | 1 | 18.657 | 0.46 | Glu | 1 |
| 20.74 | 1.24 | Pro | 1 | 20.883 | 0.39 | Pro | 1 |
| 25.79 | 0.07 | Gly | | 26.207 | 0.06 | Gly | |
| 27.2 | 2.43 | Ala | 2 | 27.563 | 0.80 | Ala | 2 |
| 31.49 | 1.82 | Val | 2 | 31.91 | 0.53 | Val | 2 |
| 35.57 | 0.01 | Met | | | | | |
| 40.51 | 0.24 | Ile | | 41.167 | 0.14 | Ile | |
| 42.32 | 0.04 | Leu | | 42.967 | 0.02 | Leu | |
| 45.36 | 0.01 | Tyr | | 46.31 | 0.01 | Tyr | |
| 48.3 | 0.04 | Phe | | 49.347 | 0.01 | Phe | |
| 53.71 | 2.67 | GalNH2 | 2 | 55.37 | 0.76 | GalNH2 | 2 |
| 54.56 | 0.00 | | | | | | |
| 62.61 | 0.08 | Lys | | 64.613 | 0.01 | Lys | |
| 65.56 | 1.98 | NH3 | | 67.41 | 0.97 | NH3 | |
| | | | | 69.34 | 0.00 | His | |
| 79.41 | 0.02 | Arg | | 80.367 | 0.00 | Arg | |

A

B

A
M28

B
M26

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile

<400> SEQUENCE: 1

Val Xaa Glu Thr Thr Ala Ala Pro
1               5

<210> SEQ ID NO 2
<211> LENGTH: 8
<212> TYPE: PRT
<213> ORGANISM: Homo sapiens

<400> SEQUENCE: 2

Thr Thr Ser Thr Thr Ser Ala Pro
1               5

<210> SEQ ID NO 3
<211> LENGTH: 8
<212> TYPE: PRT
<213> ORGANISM: Chrysaora melanaster
<220> FEATURE:
<221> NAME/KEY: MOD_RES
<222> LOCATION: (3)..(4)
<223> OTHER INFORMATION: Any amino acid

<400> SEQUENCE: 3

Val Glu Xaa Xaa Ala Ala Pro Val
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Val Glu Thr Thr Ala Ala Pro
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(5)
<223> OTHER INFORMATION: Any amino acid
```

```
<400> SEQUENCE: 5

Val Xaa Glu Xaa Xaa Ala Ala Pro
1               5

<210> SEQ ID NO 6
<211> LENGTH: 8
<212> TYPE: PRT
<213> ORGANISM: Aurelia aurita
<220> FEATURE:
<221> NAME/KEY: MOD_RES
<222> LOCATION: (4)..(5)
<223> OTHER INFORMATION: Any amino acid

<400> SEQUENCE: 6

Val Val Glu Xaa Xaa Ala Ala Pro
1               5

<210> SEQ ID NO 7
<211> LENGTH: 8
<212> TYPE: PRT
<213> ORGANISM: Aurelia aurita
<220> FEATURE:
<221> NAME/KEY: MOD_RES
<222> LOCATION: (4)..(5)
<223> OTHER INFORMATION: Any amino acid

<400> SEQUENCE: 7

Val Ile Glu Xaa Xaa Ala Ala Pro
1               5

<210> SEQ ID NO 8
<211> LENGTH: 8
<212> TYPE: PRT
<213> ORGANISM: Chrysaora melanaster
<220> FEATURE:
<221> NAME/KEY: MOD_RES
<222> LOCATION: (3)..(4)
<223> OTHER INFORMATION: Any amino acid

<400> SEQUENCE: 8

Ile Glu Xaa Xaa Ala Ala Pro Val
1               5
```

MUCIN-TYPE GLYCOPROTEIN AND USE THEREOF

CROSS-REFERENCE TO RELATED APPLICATIONS

The present application is a 35 U.S.C. §371 National Stage patent application of International patent application PCT/JP2006/315939, filed on Aug. 11, 2006, which claims priority to Japanese patent application JP 2005-234108, filed on Aug. 12, 2005.

TECHNICAL FIELD

The present invention relates to a novel mucin-type glycoprotein and to a method for producing the same. The present invention also relates to a composition comprising the novel mucin-type glycoprotein. Furthermore, the present invention relates to a molecular weight marker comprising the novel mucin-type glycoprotein.

BACKGROUND OF THE INVENTION

Among glycoproteins, high molecular glycoprotein compounds, in which a sugar chain comprising approximately one to ten monosaccharides is bound via an O-glycoside bond at regular intervals to a peptide chain having a simple repeat structure, are collectively called mucins. Various mucins are present in cells or as components in plant and animal mucus in the natural world and are known to play various important roles in living systems. Moreover, mucins from plants and animals and contained in mucus components in foods are known to give important biological effects in life activity or in digestion and absorption processes, even when ingested as foods.

Approximately ten kinds of mucins have been identified in humans to date. These mucins are distributed and present mainly in mucosal portions such as saliva and gastric mucosa. Mucosal tissues formed by these mucins exhibit biological roles such as antibacterial effects as an extracellular matrix, by which viral infections or the like are blocked, in addition to physical effects such as the moisture retention, protection, and lubrication of cells and tissues (H. Nakata, Diversity of Mucin and Mucin-type Sugar Chain and Its Meaning: Understandable Glycobiology in Post-Genomic Era, Wakaru Jikken-Igaku Series (Understandable Experimental Medicine) (in Japanese), N. Taniguchi ed., Chapter 3, Yodosha Co., Ltd., 2002; K. Hotta, K. Ishihara, Search for Attractiveness of Gastric Mucus: Elucidation of Mucin using Newest Approach (in Japanese), Medical View Co., Ltd., 1999).

The physiological effects of these mucins do not always result from specific chemical reactions. Their physiological effects are also considered to be derived from their physical properties as substance, i.e., morphology including plasticity, viscosity, moisturizing properties, and so on, and from their ability to recognize a wide variety of molecules (e.g., lectin) due to the amorphous sugar chain portion bound to the peptide chain having a three-dimensional structure. Thus, the physical properties and three-dimensional structure of the polymer portion comprising of the peptide chain of mucins as well as the ability of molecular recognition by the amorphous sugar chain portion are needed to exert their functions.

On the other hand, such compounds constituting partial or main components in mucosa or an extracellular matrix exert their effects even when ingested from outside. Therefore, these compounds have been considered currently to have a great advantage that they may be artificially produced and supplied to the market as pharmaceuticals, cosmetics, foods, and so on (JP 8-269091A (1996)). Among sugar chain compounds, ahead of all others, chondroitin, chondroitin sulfate, and hyaluronic acid, etc., main components of an extracellular matrix, have been extracted and purified from various raw materials and provided into the market as foods, pharmaceuticals, cosmetics, and so on. However, mucins are taken merely dietary from, for example, some foods (aroid, okra, and Jew's-ear) or animals (cattle and pigs) (see JP 7-33623A (1995); JP 8-256788A (1996); JP 6-199900A (1994); JP 5-310799A (1993); and JP 7-126292A (1995)), and have not been supplied yet as compounds on a large-scale basis and in large amounts.

The glycoproteins including mucins have the molecular recognition ability and are expected to be useful in various use such as in pharmaceuticals. Nevertheless, an appropriate method for synthesizing them has not been found. In some cases, genes encoding the peptide sequences have been identified. However, approaches such as gene transfer or cloning have been attained with little success due to the difficulty for introduction of sugar chains after peptide chain synthesis (Polysaccharide Separation/Purification Method, Biological and Chemical Experimental Methods 20 (in Japanese), edited by K. Matsuda, Japanese Scientific Societies Press, 1987). For most glycoproteins, their synthetic methods have no excepting an approach involving synthesizing only the peptide chain by use of E. coli or the like and sequentially introducing sugar chains thereinto (see WO 96/13516). Such an approach has a disadvantage that they are unsuitable for large-scale production.

Glycoproteins include those with mucin-type sugar chains or those with asparagine-type sugar chains. Chaperone molecules which mediate binding of sugar chain are identified for some asparagine-type sugar chains, and binding sites of such sugar chains have been identified in some cases. Nevertheless, it is difficult to specify the sites of sugar chain introduction upon synthesis. Even if sugar chains can be introduced sequentially into an already synthesized peptide chain, it is expected that the higher order structure of the peptide chain is largely altered due to binding of sugar. Thus, there is no guarantee that the peptide chain forms the native higher order structure by refolding.

Meanwhile, restricted to mucin-type glycoproteins, the peptide chain forms a higher order structure by folding and then undergoes sugar chain modification. Therefore, the sugar chain can be bound to the peptide chain, with the maintained three-dimensional structure and functions of the protein. Thus, the sugar chain can be introduced with little loss of the whole higher order structure of the peptide chain (M. Fukuda, Mucin-type Sugar Chain, pp. 35-56, Y. Kohata, S. Hakomori, and K. Nagai ed., "Diverse World of Sugar Chain" (in Japanese), Kodansha Scientific, Ltd., 1993). Thus, mucin-type glycoproteins seems to have advantages in use for drug development. However, the amino acid sequences of binding sites in currently known mucin-type glycoproteins are not found to have any rule, and this makes it difficult to introduce a sugar chain at an intended position. Moreover, although the mucin-type glycoproteins have a relatively simple primary structure, it is also difficult to synthesize the whole mucin-type glycoproteins by a synthetic organic chemistry approach. For these reasons, it seems that an industrial approach for supplying mucin-type glycoproteins in large amounts has not been developed yet, although mucin-type glycoproteins have many superior characteristics.

A gel filtration method, also called Size Exclusion Chromatography (SEC), has been used widely for a long time as a convenient and accurate approach for measuring the molecular weights of polymer compounds. This method has been used not only as analysis using open columns but also as high-performance liquid chromatography and also allows fractionation based on molecular weights, particularly, automatic fractionation (A. Fallon, R. F. G. Booth, L. D. Bell, translated by T. Osawa, High-Performance Liquid Chromatography, Biochemical Experimental Method 9 (in Japanese), Chapter 5, Tokyo Kagaku Dojin Co., Ltd. 1989). However, it is technically difficult to determine the absolute value of the molecular weight of an unknown substance only by performing these measurements. Specifically, there are two requirements that a column carrier, with which it is assured that gel filtration can be done with good reproducibility according to a theoretical calibration curve, is used and that an accurate standard molecular weight marker is used. Thus, the combination of a test substance and a column carrier and the combination of a test substance and a molecular weight marker must be chosen sufficiently carefully.

A measurement method using a time-of-flight mass spectrometer (MALDI-TOF MS) has been spread in recent years as such an approach for absolute molecular weight measurement. This approach can achieve absolute measurement by which the molecular weights of polymer compounds are determined accurately. However, the apparatus for this method is much more expensive than liquid chromatographs. It is actually impossible to spread the apparatus into all chemical synthesis laboratories, factories, medical facilities, and so on. Analysis may be conducted centrally at one location in which the expensive equipment is placed or may be outsourced. However, laboratories, which require quick feedback and desire rapid measurement, still utilize analysis using SEC with frequency. In such a case, it is preferred that a common substance that can be measured by both MALDI-TOF MS and SEC should be used as a standard for absolute molecular weight measurement.

As long as the SEC approach is used, a standard substance used in the combination of a test substance and a molecular weight marker must be as similar in physical property to a test substance as possible. The principle of SEC is that separation is achieved on the basis of a solute size (molecular weight) by use of molecular sieve effects brought by a polymer filler network. Therefore, the separation depends on physical properties such as size or shape but not on chemical properties that give the interaction between the solute and a stationary phase. Specifically, substances similar in hydrodynamic radius and shape of a polymer in a solvent (mobile phase) need to be selected for use as the standard. SEC users commonly select and utilize, from catalogues, polymer molecular weight markers that take conformation as similar to one another as possible. However, for previously forming a marker that has narrow molecular weight distribution and has a molecular weight controlled to some extent, it is most convenient to use a synthetic polymer for which a method for controlling a polymerization process is known. Thus, a very limited number of substances are commercially available as molecular weight markers. Specifically, only polymers having a linear structure, such as polystyrene, polymethyl methacrylate (PMMA), polyethylene, polyethylene glycol, polyethylene oxide, polyacrylic acid, and pullulan, are now on the market (e.g., JP Patent No. 3012917 (JP 10-60005A (1998))). Under such circumstances, it is impossible to cover all of many polymer compounds.

Among others, glycoproteins (e.g., enzymes, mucins, and hormones) whose physiological actions have received attention in recent years have no appropriate standard molecular weight markers. The glycoproteins are universally distributed in the natural world and are present in larger numbers than proteins free of sugars. Some of them have plural sugar chains bound to the peptide chain and exhibit a brush-like form, while glycoproteins with only one sugar chain bound per molecule are present and even these have a very bulky sugar chain portion covering the surface of the molecule. When such a glycoprotein is analyzed using SEC for separation on the basis of a "molecular size and shape", it is obvious that the use of conventional molecular weight markers having a linear structure is inappropriate. For example, pullulan, a polysaccharide, has been used as a molecular weight marker for such a reason that it contains sugars. However, there has been no guarantee so far that such a molecular weight marker provides an accurate molecular weight. Under present circumstances, the evaluated molecular weight, which may however be wrong, only indicates the relative relationship with other markers used. Specifically, the estimation of molecular weights only by SEC was basically inaccurate and required confirmation using another method.

Electrophoretic methods such as SDS-PAGE are also protein separation analysis approaches that can be used conveniently in laboratories. Appropriate molecular weight markers may also be needed and are generally used for such analytical approach, as in SEC. Such molecular weight markers are also used in the fields of various common biochemical analyses other than SEC and electrophoretic methods.

Jellyfishes, that are seen predominantly in the summer period, sometimes are seen in a large number and may therefore significantly lower the efficiency or economic effects of the intake/drainage system in nuclear power or thermal power plants, of the intake/drainage system for industrial water in a variety of factories facing the ocean, of harbors, of fishery with fishing nets such as fixed shore nets, and so on. Particularly, moon jelly (*Aurelia aurita*) or the like, which has a poor swimming ability, must be eradicated actively, particularly when seen in a large number. Large jellyfishes such as Echizen-kurage jellyfish (*Nemopilema nomurai*), when seen in a large number, require, due to their weights, massive operation for pulling them up for evacuation from the ocean using heavy machineries or the like. As a result of such operations, jellyfishes are pulled up from the ocean in large amounts at once. However, the jellyfishes once pulled up are regarded as wastes under current Japanese law and prohibited from being disposed of again into the ocean. Therefore, they must be landed and accumulated. Methods for utilizing such accumulated jellyfishes as foods or as fertilizers have been proposed (e.g., JP 2004-99513A; JP 2003-321497A; JP 2001-178492A; JP 2002-370991A; WO 95/17428; JP 2002-143824A; JP 6-217737A (1994); and V. Schmidt, A. Bally, K. Beck, M. Haller, W. K. Schlage, C. Weber "The extracellular matrix (mesoglea) of hydrozoan jellyfish and its ability to support cell adhesion and spreading. Hydrobiologia 216-217, pp. 3-10 (1997)). However, due to the absence of other effective ways to use them, disposal of them for the reason of environmental protection places an enormous economic burden on corporations or municipalities in charge. For obtaining costs for disposal, it is desired that costs for promoting the disposal of the residue should be recovered by isolating expensive valuables from them even in small amounts. However, effective solutions therefor have not been obtained yet.

The amount of moon jelly (*Aurelia aurita*) seen in a large number is estimated by air observation or the like and allegedly reaches several hundreds of thousands of tons per gulf in some cases (T. Yasuda ed., "Marine UFO Jellyfish" (in Japanese), pp. 41-77 VII Emergence and Distribution, Kouseisha Kouseikaku Co., Ltd., 2003). Since jellyfishes are present as marine resources with rich abundance on Earth, not only are the accumulated wastes used, but the utilization thereof by active harvest can be taken into consideration.

DISCLOSURE OF THE INVENTION

Problems to be Solved by the Invention

An object of the present invention is to provide a mucin-type glycoprotein that can be used in medical cares, foods, and so on by large-scale production and is useful as a substitute substance for human mucin, a method for producing the same, and use thereof. Moreover, another object of the present invention is to provide a molecular weight marker that can be used in the molecular weight measurement of glycoproteins.

Means for Solving the Problems

As a result of diligent studies for attaining the objects, the present inventors have now successfully isolated and purified a novel mucin-type glycoprotein from jellyfishes and have also found that the mucin-type glycoprotein can serve as a substitute substance for human mucin, as a result of analyzing the structure and properties of the mucin-type glycoprotein. Moreover, the present inventors have now found that the mucin-type glycoproteins from jellyfishes can be used as molecular weight markers for the molecular weight measurement of glycoproteins, because this mucin-type glycoproteins have a wide distribution of molecular weights. Based on these findings, the present invention has been completed.

Specifically, the present invention relates to the following (1) to (9):

(1) A mucin-type glycoprotein having a repeat structure which comprises three or more repeating units each having an amino acid sequence represented by formula I (SEQ ID NO: 1):

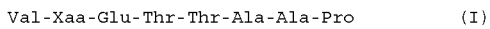

```
Val-Xaa-Glu-Thr-Thr-Ala-Ala-Pro         (I)
```

[wherein Xaa represents Val or Ile], wherein one or more amino acid residues in the structure are bound to a sugar chain consisting of one or more monosaccharides.

When the mucin-type glycoprotein is present in the natural world, the glycoprotein is expected to have approximately 3 to 2000 repeating units, preferably 3 to 700 repeating units. Furthermore, approximately 50% of main components have a repeat structure comprising 40 to 180 repeating units. In this context, the repeating units may be bound together directly or may be bound via linker(s).

For the mucin-type glycoprotein, it is preferred that the amino acid residue bound to a sugar chain is threonine (Thr). For example, 98% or more of the amino acid residues bound to a sugar chain may be threonine (Thr).

In the mucin-type glycoprotein, the sugar chain comprises, for example, but not limited to, a monosaccharide selected from the group consisting of N-acetylgalactosamine, galactose, N-acetylglucosamine, sialic acid, arabinose, and fucose. Preferably, the sugar chain comprises N-acetylgalactosamine. Yet preferably, the sugar chain comprises N-acetylgalactosamine and galactose.

In the mucin-type glycoprotein, one or several amino acids, for example, Val, may be deleted at the N-terminus of the repeating structure.

It is preferred that the mucin-type glycoprotein is extracted from jellyfishes, for example, moon jelly (*Aurelia aurita*), Echizen-kurage jellyfish (*Nemopilema nomurai*), or brown jellyfish (*Chrysaora melanaster*).

(2) A mucin-type glycoprotein produced by a method comprising the following steps of:
cutting the solid portions of a jellyfish;
extracting the cuttings (or fragments) of the jellyfish with a salt solution;
separating crude mucin from the extract by centrifugation and dialysis; and
purifying a mucin-type glycoprotein.

(3) A method for producing a mucin-type glycoprotein, comprising the following steps of:
cutting the solid portions of a jellyfish;
extracting the cuttings (or fragments) of the jellyfish with a salt solution;
separating crude mucin from the extract by centrifugation and dialysis; and
purifying a mucin-type glycoprotein, wherein all of the steps are performed at 0 to 25° C.

For the method for producing a mucin-type glycoprotein, it is preferred that all of the steps are performed at a low temperature close to the ice temperature (0 to 25° C., preferably 4° C.) without heating.

(4) A composition comprising any of the above mucin-type glycoproteins.

The composition is used in, for example, cells and tissue protection, the moisture retention or absorption of skin surface, health promotion, drug administration, disease treatment or prevention, or antibacterial applications. Moreover, it is preferred that the composition is in a form of an aqueous solution, membrane, or resin.

(5) A method for modifying a mucin-type glycoprotein, characterized by modifying the sugar chain of any of the above mucin-type glycoproteins by the action of glycosyltransferase.

(6) A protein having a repeat structure which comprises 1 to 2000 repeating units each having an amino acid sequence represented by formula I (SEQ ID NO: 1):

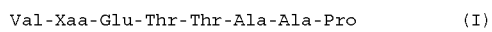

```
Val-Xaa-Glu-Thr-Thr-Ala-Ala-Pro         (I)
```

[wherein Xaa represents Val or Ile].

(7) A method for producing a glycoprotein, binding at least one amino acid residues in the protein to a sugar chain comprising one or more monosaccharides.

(8) A molecular weight marker comprising a mucin-type glycoprotein and having medians of molecular weight distribution and molecular distribution as measured by an absolute molecular weight determining method, the mucin-type glycoprotein having a repeat structure which comprises 3 to 2000 repeating units each having an amino acid sequence represented by formula I (SEQ ID NO: 1):

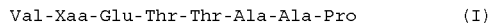

```
Val-Xaa-Glu-Thr-Thr-Ala-Ala-Pro         (I)
```

[wherein Xaa represents Val or Ile], wherein one or more amino acid residues in the structure are bound to a sugar chain consisting of one or more monosaccharides.

The molecular weight markers may have a molecular weight ranging from 10 to 1,400 kDa. Moreover, it is preferred that the molecular weight markers are freeze-dried.

(9) A method for producing a molecular weight marker, comprising the following steps of:
subjecting a mucin-type glycoprotein to size exclusion chromatography for fractionation, the mucin-type glycoprotein having a repeat structure which comprises 3 to 2000 repeating units each having an amino acid sequence represented by formula I (SEQ ID NO: 1):

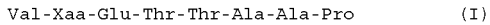

[wherein Xaa represents Val or Ile], wherein one or more amino acid residues in the structure are bound to a sugar chain consisting of one or more monosaccharides;

collecting and purifying the fractions; and measuring absolute molecular weights of the purified fractions.

The method for producing a molecular weight marker may further comprise the step of freeze-drying the purified fractions.

Advantage of the Invention

The present invention provides a novel mucin-type glycoprotein. The mucin-type glycoprotein can be used as, for example, a substitute substance for human mucin and is useful in fields such as pharmaceutical, agricultural, and food fields. Moreover, the mucin-type glycoprotein is produced easily in large amounts from jellyfishes and is therefore superior as economical and environmental preservation techniques.

The present invention also provides molecular weight markers comprising mucin-type glycoproteins. The molecular weight markers have branched polymer chains obtained from natural polymers. The use of the present molecular weight markers allows for the accurate determination of the molecular weights of branched polymers such as glycoproteins.

BRIEF DESCRIPTION OF THE DRAWINGS

FIG. 4 shows the results of analyzing the constituent amino acids of purified mucin-type glycoproteins from moon jelly (*Aurelia aurita*) and brown jellyfish (*Chrysaora melanaster*) with an automatic amino acid analyzer;

FIG. 5-1 shows the result of analyzing the amino acid sequence of a purified mucin-type glycoprotein from moon jelly (*Aurelia aurita*) by a pulse liquid phase method;

FIG. 5-2 shows the result of analyzing the amino acid sequence of a purified mucin-type glycoprotein from brown jellyfish (*Chrysaora melanaster*) by a pulse liquid phase method;

FIG. 6-1 shows the result of a monosaccharide analysis of a purified mucin-type glycoprotein from moon jelly (*Aurelia aurita*);

FIG. 6-2 shows the result of a monosaccharide analysis of a purified mucin-type glycoprotein from brown jellyfish (*Chrysaora melanaster*);

FIG. 10-1 shows the result of a molecular weight measurement of each fraction by a MALDI-TOF MS method;

FIG. 10-2 shows the result of a molecular weight measurement of each fraction by a MALDI-TOF MS method;

FIG. 10-3 shows the result of a molecular weight measurement of each fraction by a MALDI-TOF MS method.

BEST MODE FOR CARRYING OUT THE INVENTION

Figure 1:
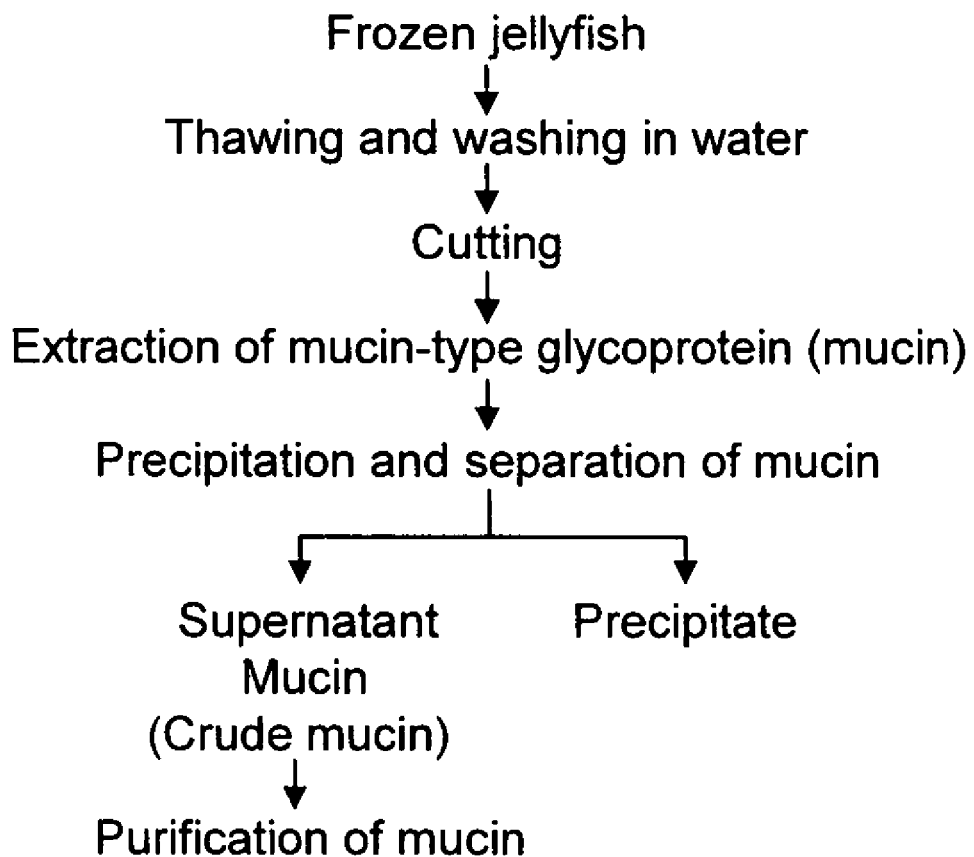
FIG. 1 shows the summary of procedures of treating jellyfish for isolating a mucin-type glycoprotein.

Hereinafter, the present invention will be described in detail. The present application claims the priority of Japanese Patent Application No. 2005-234108 filed on Aug. 12, 2005 and encompasses the contents described in the specification and/or drawings of the patent application.

The present invention provides a novel mucin-type glycoprotein. The mucin-type glycoprotein refers to a glycoprotein that has a repeat structure comprising particular amino acid sequences as units and has a mucin-type sugar chain (also called an O-linked sugar chain). In the mucin-type glycoprotein, N-acetylgalactosamine is generally bound via an O-glycoside bond to the hydroxyl group of a serine or threonine residue in the protein, and a monosaccharide is in turn bound to the N-acetylgalactosamine to form a sugar chain.

The structure and properties of the mucin-type glycoprotein according to the present invention (the present mucin-type glycoprotein) will be described below. The present mucin-type glycoprotein has a repeat structure comprising three or more repeating units having an amino acid sequence represented by the following formula I (SEQ ID NO: 1):

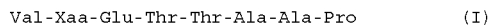

[wherein Xaa represents Val or Ile].

The mucin-type glycoprotein is a polymer compound having an undefined molecular weight as its characteristics. Even if mucin-type glycoproteins are obtained from the same species and obtained in the same experiment, the number of the repeating units differs among the individual molecules. As a result of gel filtration analysis, the molecular weight of the mucin-type glycoprotein isolated by the present inventors was 10 to 1400 kDa, when the result of the gel filtration analysis was corrected by use of a number average obtained by amino acid sequence analysis. Therefore, also taking a sugar chain structure described later into consideration, it is expected that polymers with about three times larger molecular weight than those obtained by the experiment (having approximately 3 to 700 repeating units) may be present in the natural world. Even such larger mucin-type glycoproteins are not likely to largely differ from smaller one in physical property or function. Thus, the estimated number of the repeating units is approximately 3 to 2000, preferably 3 to 700. In this context, the estimated number of the repeating units is, for example, approximately 3 in a mucin-type glycoprotein having a molecular weight of approximately 4.5 kDa and approximately 40 in a mucin-type glycoprotein having a molecular weight of approximately 750 kDa, assuming that all of the threonine (Thr) residues are bound to a sugar chain and the sugar chain portion is the most typical sequence -GalNAc-Gal. In the present specification, the number of the repeating units is calculated from a molecular weight on the basis of the same assumption, unless otherwise specified.

The gel filtration chromatogram of the mucin-type glycoprotein obtained from a jellyfish in the experiment (Example 6) shows that 50% of the total amount has a molecular weight of 60 kDa to 270 kDa, that is, 40 to 180 repeat units, as a result of correction by the value obtained as an absolute molecular weight using MALDI-TOF. Similarly, the chromatogram shows that components having a molecular weight of 90 kDa to 210 kDa, that is, 60 to 150 repeat units account for 30% of the total amount.

The repeating units may be bound together directly or may be bound via linker(s). The linker may be, for example, but not limited to, an S—S bond using cysteine.

Moreover, the results of the analyses shown in Examples 3 and 4 show that the isolated mucin-type glycoprotein contained different amino acids from the repeat structure mentioned above. However, the amount thereof was 5% or lower in terms of a molar ratio. These additional amino acids are probably from impurities or present mainly at the terminus or in the junction of the repeating units and serve as portions that impart additional functions such as in-vivo fixation functions attributed to membrane binding. Thus, the present mucin-type glycoprotein may contain additional amino acids, in addition to the repeat structure, without influencing its functions as mucin (e.g., viscosity, antibacterial properties, and moisturizing properties). Furthermore, the repeating units in the repeat structure may have amino acid shift. Specifically, as shown in Example 4, a mucin-type glycoprotein from brown jellyfish (*Chrysaora melanaster*) has the repeating units of VEXXAAPV (SEQ ID NO: 3), which are shifted by one amino acid from the repeating units represented by the formula I. Thus, the present mucin-type glycoprotein also encompasses a protein comprising the repeating units having amino acid shift as a result of deletion of one or several amino acids present at the N-terminus of the repeat structure. Preferably, such a protein is a mucin-type glycoprotein in which Val present at the N-terminus of the repeat structure is deleted.

In the present mucin-type glycoprotein, one or more amino acid residues in the repeat structure are bound to a sugar chain consisting of one or more monosaccharides. The amino acid residue bound to a sugar chain is not particularly limited. It is preferred that threonine (Thr) residue is bound to a sugar chain. For example, in the present mucin-type glycoprotein, 98 to 100% of all the amino acid residues bound to a sugar chain may be threonine (Thr). Moreover, the mucin-type glycoprotein is a polymer compound having an undefined molecular weight as its characteristics, as described above. Therefore, the number of the amino acid residues bound to a sugar chain differs among individual molecules. However, it is expected that almost all of two threonine residues in the repeat unit are bound to a sugar chain. Thus, the number of bound sugar chains in the present mucin-type glycoprotein differs depending on the number of the repeating units.

The monosaccharide constituting the sugar chain is not particularly limited, as long as it is that found in general mucin-type glycoproteins. Examples thereof include N-acetylgalactosamine, galactose, N-acetylglucosamine, sialic acid, arabinose, and fucose. It is particularly preferred that the sugar chain comprises N-acetylgalactosamine and/or galactose. Specifically, it is preferred that the threonine (Thr) residues in the repeating units is bound to N-acetylgalactosamine and galactose to have the structure of Thr-GalNAc-Gal or is bound to only N-acetylgalactosamine to have the structure of Thr-GalNAc. For example, such a mucin-type glycoprotein is represented by the following formula (SEQ ID NO: 4):

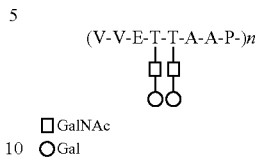

□ GalNAc
○ Gal

[wherein Gal represented by an open circle may be deleted].

The sugar chain comprises 1 to 10, preferably 1 to 8, more preferably 1 to 5 monosaccharides linked in a linear or branched form. Due to the characteristics of the mucin-type glycoprotein of undefined molecular weight, the number, type, structure, size, and so on of the sugar chain contained in the present mucin-type glycoprotein differ among individual mucin-type glycoproteins. Sugar chains contained in one mucin-type glycoprotein may also differ from each other. As described in Examples 2 to 6, mucin-type glycoproteins extracted from moon jelly (*Aurelia aurita*) and brown jellyfish (*Chrysaora melanaster*) had, in their comparison, totally the same repeating portions in the peptide chains and differed only in the types and component ratios of constituent sugars in the sugar chain portions. Moreover, these mucin-type glycoproteins seem to be present for the same purposes in the natural world in which moon jelly and brown jellyfish are present. It can be considered that the mucin-type glycoproteins in these two jellyfishes do not largely differ from each other in their function. Therefore, the sugar chain structure does not alter the main properties of the present mucin-type glycoprotein and can rather be expected to play a role in finely controlling specificity. Thus, even a mucin-type glycoprotein differing in sugar chain portion but having the repeat structure of the peptide chain is incorporated within the scope of the present invention.

The sugar chain in the present mucin-type glycoprotein is converted by glycosyltransferase present in vivo. Thus, the sugar chain in the present mucin-type glycoprotein is not limited to those described above and even a mucin-type glycoprotein having a modified sugar chain are incorporated within the scope of the present invention, as long as it has a repeat structure comprising three or more repeating units having an amino acid sequence represented by the formula I, wherein one or more amino acid residues in the structure are bound to a sugar chain consisting of one or more monosaccharides. This is because such a mucin-type glycoprotein is expected to have relevant functions and properties.

The mucin-type glycoprotein comprising a sugar chain modified by glycosyltransferase is likely to have novel usefulness by virtue of further ability of molecular recognition imparted thereto by sugar modification. Thus, the present invention provides a method for modifying the sugar chain of the present mucin-type glycoprotein by the action of glycosyltransferase. Examples of glycosyltransferase that may be used include glycosyltransferase, galactosyltransferase, N-acetylgalactosaminyltransferase, sialyltransferase, and fucosyl-transferase. An approach for modifying a sugar chain using glycosyltransferase is known in the art and any method can be used for this purpose.

The present mucin-type glycoprotein is a compound that has linkages of Thr-GalNAc-Gal, called the type 1 core in connection with mucin-type glycoproteins, and/or linkages having a simple structure of Thr-GalNAc. Therefore, the present mucin-type glycoprotein is characterized in that it can be used as a raw material for converting the sugar chain portion to a desired sugar chain by using a known enzyme. For example, the sialic acid can be bound to galactose by the action of commercially available a2→3NeuAc transferase thereon, as in reactions occurring in normal lymphocytes.

In addition, the whole or partial portion of the sugar chain can be removed to thereby limit the action of the mucin-type glycoprotein, enhance a particular efficacy, or give a novel action. Furthermore, partially added sugars can be removed to enhance homogeneity as a substance. Thus, the sugar chain modification provided by the present invention also encompasses the release of a particular sugar from the sugar chain. Examples of a sugar-releasing enzyme that may be used include glucosidase, galactosidase, N-acetylgalactosaminidase, sialidase, and fucosidase.

Converting the sugar chain portion in the present mucin-type glycoprotein to a desired sugar chain allows to control the ability of molecular recognition by the sugar chain finely such that the ability is changed from that originally possessed by the present mucin-type glycoprotein to that having desired specificity and affinity. For example, materials adhering to cells, viruses, or toxins produced thereby have currently been developed and put in practical use. These are produced by introducing various sugar chains recognizing lectin, a sugar-binding protein, into various polymer materials such as polystyrene (K. Kobayashi, Artificial Complex Sugar Chain Polymer, pp. 181-195, K. Kobayashi and S. Shoda ed., "The Recent Trends of Glycochemistry" (in Japanese), Part 2, Chapter 2.1, CMC Publishing Co., Ltd., 2005). The present mucin-type protein can also be allowed to have similar functions as such polymer material. For example, Shiga toxin produced by O-157 is known to strongly bind to a trisaccharide Galα1-4Galβ1-4Glcβ or a disaccharide Galα1-4Galβ1. Therefore, the present mucin-type protein can be allowed to have antitoxic effects on the Shiga toxin by binding an appropriate amount of these sugars thereto. A large number of sugar chains are known to have such effects. Therefore, the sugar chains having the ability of recognition are not limited. Also, targets to be recognized by the sugar chains are not limited and may be glycoproteins (e.g., lectins), toxins, agents, and so on present intracellularly or extracellularly, on cell surfaces, within cellular membranes, within or without viruses, and on virus surfaces.

The present invention also relates to a protein having a repeat structure comprising 1 to 2000 repeating units having an amino acid sequence represented by the formula I. The protein can also be bound to a sugar chain by use of glycosyltransferase in the same way as above.

The mucin-type glycoprotein of the present invention is extracted from jellyfishes. The jellyfishes refer to organisms belonging to the phylum *Cnidaria*. Typical examples thereof include *Aurelia aurita* (moon jelly) (family Ulmaridae), *Chrysaora melanaster*(brown jellyfish) (family Pelagiidae), *Aequorea coerulescens* (Owan-kurage jellyfish) (family Aequoreidae), *Nemopilema nomurai* (Echizen-kurage jellyfish) (family Stomolophidae), *Charybdea rastoni* (Andon-kurage jellyfish) (family Carybdeidae), *Rhopilema esculenta* (Bizen-kurage jellyfish) (family Rhizostomidae), and *Chiropsalmus quadrigatus* (Habu-kurage jellyfish) (family Chirodropidae). It is preferred that the jellyfishes used for producing the present mucin-type glycoprotein are those which have been confirmed to be safe for humans and animals. Such jellyfishes may be, for example, but not limited to, *Aurelia aurita*, *Rhopilema esculenta*, and *Nemopilema nomurai*, which have already been used as foods. The jellyfishes can be used in various states. For example, raw, frozen, dried, and salt-cured jellyfishes can be used. Moreover, the part of a jellyfish used to extract the mucin-type glycoprotein is not particularly limited. For example, epidermis, oral arms, gastric corpus, body fluids, and the like, or liquid components generated from cryopreservation or storage at room temperature can be used.

A method for producing a mucin-type glycoprotein using a frozen jellyfish will be taken as one example, and its summary is shown in FIG. 1. First, a frozen jellyfish is thawed and washed in water. For example, when a raw or dried jellyfish is used, the jellyfish is washed in water in the same way. Solid matter and liquid are separated by centrifugation, if necessary.

Subsequently, the jellyfish (solid matter) was cut into fragments of approximately 0.5 mm to 2 cm square, preferably approximately 1 cm square, with scissors. This cutting or disruption method should be suitable for the state of a sample used, the performance of a centrifuge used in subsequent processes, and so on. When finer fragments are needed, an appropriate cutting-disruption method such as an automatic mixer can be used. When the epidermis of the sample starts to be degraded or the sample loses freshness with soft fluid portions, it is preferred that degreasing and dehydration are performed by acetone treatment. After this acetone treatment, the dehydrated sample should be swollen again with water for use.

When body fluids or liquid components generated from cryopreservation or storage at room temperature are used, the production method can proceed to the next step without performing the steps described above.

Next, the solid sample is added to a salt solution and subjected to extraction by shaking. The salt solution used comprises, but not limited, NaCl, KCl, MgCl$_2$, CaCl$_2$, ammonium oxalate, LiBr, EDTA, or a neutral buffer solution (e.g., phosphate or citrate buffer solution), preferably 0.2 to 3.5% NaCl, particularly preferably 0.2% NaCl. In this context, when the jellyfish sample contains a large amount of salts, the amount of the salt added thereto is also adjusted such that the final salt concentration falls within this rang. The extraction temperature is approximately 2 to 25° C., preferably approximately 4° C.

After extraction, the solution is centrifuged at 1000 to 10000 g, preferably, the fastest speed of 10000 g, for 5 to 20 minutes with the temperature kept. To the extracts, ethanol is added to give precipitates. This solution is left standing overnight at approximately 0 to 4° C. and then centrifuged at 1000 to 10000 g, preferably 10000 g, for 5 to 20 minutes with the temperature kept.

The obtained precipitate is dissolved in a small amount of water, and the solution is centrifuged at 1000 to 10000 g, preferably 10000 g, for 5 to 20 minutes with the temperature kept. The supernatant is then removed therefrom and purified by dialysis treatment. The obtained product is a crude mucin-type glycoprotein, and this crude mucin-type glycoprotein is then freeze-dried.

In mucin-type glycoprotein purification, biochemical methods generally used in protein isolation and purification, for example, fractionation using an organic solvent, ultrafiltration methods, a variety of electrophoretic methods, a variety of dialysis methods, gel chromatography, hydrophobic chromatography, reverse-phase chromatography, ion-exchange chromatography, and affinity chromatography, can be used alone or optionally in combination. For example, fractions around a main peak can be obtained by ion-exchange liquid chromatography, as shown in Example 2, to purify the present mucin-type glycoprotein.

In this context, it is preferred that the production of the present mucin-type glycoprotein comprises no heating step. For example, the production of the present mucin-type glycoprotein is performed at 25° C. or lower, preferably at 0 to 25° C., more preferably at 4° C.

The method for producing the present mucin-type glycoprotein is an efficient method based on extraction from jellyfishes and further has the advantage that it can introduce mucin-type glycoproteins in large amounts to the market by an inexpensive production method, for example, by using jellyfish wastes resulted from the aquaculture of jellyfishes or in harbors or the fishing industry.

By comparing the present mucin-type glycoprotein with known mucin glycoproteins, it has been appeared that the present mucin-type glycoprotein is similar to a human mucin-type glycoprotein MUC5AC also having a repeat structure comprising eight residues (H. Nakata, Diversity of Mucin and Mucin-type Sugar Chain and Its Meaning: Understandable Glycobiology in Post-Genomic Era, Wakaru Jikken-Igaku Series (Understandable Experimental Medicine) (in Japanese), N. Taniguchi ed., Chapter 3, Yodosha Co., Ltd., 2002; K, Hotta, K. Ishihara, Search for Attractiveness of Gastric Mucus: Elucidation of Mucin using Newest Approach (in Japanese), Medical View Co., Ltd., 1999). This human mucin-type glycoprotein is present mainly in respiratory tracts and gastric mucosa. The amino acid sequence of the repeating unit in this protein is shown in the following formula II (SEQ ID NO: 2) together with that of the present mucin-type glycoprotein (formula I) (SEQ ID NO: 1):

```
The present mucin-type glycoprotein:
Val-Val-Glu-Thr-Thr-Ala-Ala-Pro (I)
    (Ile)

Human MUC5AC:
Thr-Thr-Ser-Thr-Thr-Ser-Ala-Pro (II)
 1   2   3   4   5   6   7   8
```

These amino acid sequences, in their comparison, are identical on the 4th, 5th, 7th, and 8th amino acids of the eight residues. While only Thr of the 4th and 5th residues can serve as sugar chain-binding sites in the present mucin-type glycoprotein, the 1st, 2nd, 3rd, 4th, 5th, and 6th amino acids (Ser or Thr) can serve as sugar chain-binding sites in MUC5AC. However, human MUC5AC has indeed the small quantitative ratio of sugars as a whole. This suggests that the present mucin-type glycoprotein can be used in a mixture with MUC5AC or alone as a substitute compound for MUC5AC, because the mucin-type glycoprotein seems to be similar in physical property to MUC5AC in spite of the difference of amino acid sequences and sugar chain structures. The present mucin-type glycoprotein may also be used as a substitute for other mucin-type glycoproteins.

For example, MUC5AC is commonly referred to as "gel-forming mucin". One of its main functions is to keep mucosa or mucus in a gel form. For example, the function of maintaining gastric mucosa in a gel form and preventing gastric walls from being damaged by gastric juice is allegedly important on the surface of stomach lining. The present mucin-type glycoprotein also forms a similar substance in a gel form in an aqueous solution and can therefore be used as a substitute for this role.

The present mucin-type glycoprotein has, as described below, unique physical properties attributed to the short repeat structure comprising eight residues and readily exhibits functions as a useful compound. The one-dimensional length of eight residues in the repeating unit is approximately 4 nm, and the size of the constituent unit is as very small as approximately 1 nm. Therefore, the present mucin-type glycoprotein has the advantage that it forms a sufficiently homogeneous matrix environment relative to the size of cells, viruses and bacteria in the order of 100 nm to 1 μm.

The present mucin-type glycoprotein can be used as a composition. For example, the present mucin-type glycoprotein can be mixed with, or diluted or suspended into an appropriate carrier to thereby prepare a composition. Examples of the appropriate carrier include solutions of salts (e.g., saline), lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil. Moreover, the composition may contain excipients, surfactants, dispersants, buffers, preservatives, solubilizers, soothing agents, stabilizers, tonicity agents, and so on, which are usually used.

When the composition comprising the present mucin-type glycoprotein dissolved in an aqueous solution containing a salt at a high concentration (e.g., saline) is utilized as a substitute substance for human mucus, it can have the following effects and uses:

(1) Replenishing mucosa itself, i.e., enhancing various functions (tissue protection, moisture retention, lubrication, etc.) of the mucosa;

(2) Use as a mucus substitute in treatment for replenishing mucus materials deficient due to lesions (e.g., stomach ulcer in stomach lining) or the like;

(3) Use as a drug delivery carrier for effectively supplying drugs to tissues brought in contact with mucus materials; and (4) Use as an artificial matrix with antibacterial effects that traps viruses, bacteria, and the like infectious to tissues in contact with mucus materials.

Thus, the present mucin-type glycoprotein is useful as a pharmaceutical composition for the pharmaceutical uses described above. Moreover, the present mucin-type glycoprotein can be mixed with a protein such as collagen or with a carbohydrate such as hyaluronic acid to prepare a constituent substance in an artificial extracellular matrix. Such an artificial extracellular matrix can be used as a material for forming an extracellular matrix useful in developmental and regeneration medicines.

Since the source of the present mucin-type glycoprotein is jellyfishes, the present mucin-type glycoprotein can be utilized as foods for humans and animals. Thus, the present mucin-type glycoprotein can be formulated into foods or food additives and used as a food thickener, antibacterial coating agent, or health food. The formulation into foods and food additives can be performed by a method, for example, mixing, dipping, application, or spraying.

Furthermore, mucin is known to be a moisturizing or anti-aging component. Therefore, the present mucin-type glycoprotein can also be formulated into cosmetics. Examples of the cosmetics into which the present mucin-type glycoprotein is formulated can include lotions, milky lotions, creams, and foundations. The present mucin-type glycoprotein has been confirmed to have, as shown in Example 10, moisturizing and hygroscopic abilities equivalent to those of hyaluronic acid currently known as a typical hygroscopic and moisturizing component in cosmetics.

The present mucin-type glycoprotein can be used as a starting material for synthesizing similar mucin-type glycoproteins. In the synthesis process using enzymes or usual organic synthesis reactions, the repeating unit itself (peptide chain repeated once) can be used as a tag for predicting yields in sugar chain introduction or confirming sugar chain introduction by a spectroscopy such as NMR.

The present mucin-type glycoprotein is excellent in viscosity. Therefore, an aqueous solution containing the present mucin-type glycoprotein can be molded in a membrane or resin form by drying the aqueous solution spread as a thin layer or gelling the sugar chain portion with glutaraldehyde or polycarboxylic acid. The resulted composition in a membrane or resin form is excellent in bioaffinity and biodegradability and can be used in post-surgical suture membranes, surface protection materials for artificial bone or the like, lubricants, and so on.

The composition comprising the present mucin-type glycoprotein can be used in cellular tissue protection, the moisture retention of skin surface, health promotion, drug administration, disease treatment or prevention, antibacterial applications, and so on, as described above.

Moreover, the present mucin-type glycoprotein has characteristics such as: 1) those with a wide range of molecular weight distribution are possible to be isolated; 2) it can be stored stably in a solid state as a compound; 3) samples having the same medians of molecular weight distribution and molecular distribution as each other can be purified reproducibly by fractionation according to a liquid chromatography method using an appropriate column; and 4) it can specify absolute molecular weights by conducting MALDI-TOF MS measurement on a fractionation sample having a single molecular weight. A fraction having the distinct medians of molecular weight distribution and molecular distribution can be purified and used as a molecular weight marker.

It is preferred that the mucin-type glycoprotein used as a molecular weight marker is extracted from various jellyfishes or pars thereof. For example, a mucin-type glycoprotein obtained from the epidermis of Echizen-kurage jellyfish (*Nemopilema nomurai*) has a particularly wide molecular weight distribution, as shown in, for example, Example 7. Therefore, a mucin-type glycoprotein can be isolated from the epidermis of *Nemopilema nomurai* and fractionated to thereby prepare a set of molecular weight markers having a wide molecular weight range.

The molecular weight marker comprising the present mucin-type glycoprotein can be prepared as follows: a mucin-type glycoprotein is isolated as described above and then subjected to size exclusion chromatography (SEC) under appropriate conditions using an appropriate column (see Example 7) to fractionate components of each elution time as finely as possible. Elution conditions including the column used, the composition and flow rate of the eluent, and the column temperature can be determined appropriately by those skilled in the art according to the intended molecular weight range of markers to be prepared.

Subsequently, the respective fractions are collected and purified. This purification can be performed by using, in appropriate combination, any purification methods known in the art. For example, it is preferred to perform desalting using dialysis. The purified mucin-type glycoprotein fractions having a single molecular weight can be freeze-dried and used as a solid. It is preferred that this solid sample is refrigerated at approximately 4° C. Next, each of the mucin-type glycoprotein fractions was subjected to absolute molecular weight measurement using, for example, MALDI-TOF MS method to determine their absolute molecular weights (see Example 8).

The present molecular weight markers encompass a wide range of molecular weights, as shown in Examples 6 and 7. Specifically, the present invention allows to prepare molecular weight markers having a molecular weight of approximately 10 to 1,400 kDa. The molecular weights of mucin-type glycoprotein fractions to be prepared can be determined by adjusting the elution time in the fractionation step in size exclusion chromatography. For example, fractions can be fractionated as shown in Example 8 to prepare molecular weight markers having molecular weight distribution of approximately 8 to 15 kDa (median: 11 kDa), approximately 15 to 25 kDa (median: 19 kDa), approximately 28 to 38 kDa (median: 32 kDa), approximately 45 to 55 kDa (median: 49 kDa), approximately 70 to 100 kDa (median: 86 kDa), and approximately 80 to 150 kDa (median: 110 kDa) and the distinct medians.

When the present molecular weight markers are used in the molecular weight measurement of unknown samples, it can be handled in the same way as usual molecular weight markers. In this context, it is preferred that molecular weight markers having plural molecular weights are used together. The present molecular weight markers can be used suitably in biochemical methods generally used in the molecular weight measurement of proteins, protein separation, and so on, for example, a variety of electrophoretic methods and chromatography methods (e.g., SEC). Specifically, for example, the present molecular weight markers are dissolved in an elution solvent used for solid samples and subjected to size exclusion chromatography (SEC) measurement under appropriate elution conditions. Elution conditions including the column used, the composition and flow rate of the eluent, and the column temperature differ depending on the properties of unknown samples to be measured and can be determined appropriately by those skilled in the art.

Then, a calibration curve is made using the absolute molecular weights and elution times of the molecular weight markers on the basis of the measurement results. In this procedure, it is preferred that the molecular weight markers are used in a molecular weight range that establishes the following theoretical relationship between the molecular weight and the elution time (elution volume):

$$\log(\text{molecular weight}) = A - B \times \text{elution time(elution volume)}$$

[wherein A and B represent positive numbers].

Subsequently, the unknown samples may be measured using this calibration curve (relationship between the molecular weight and the elution time).

The present molecular weight markers differ in absolute value by approximately three times from pullulan, which has been conventionally used, as shown in Example 3. In general, the results of MALDI-TOF MS are more reliable. Therefore, at least when the molecular weight distribution of glycoproteins is measured, measurement using the present molecular weight markers can be said to be more accurate. Moreover, this result is in good agreement with a value determined from a yield in consideration of Edman degradation efficiency in amino acid sequence analysis.

The mucin-type glycoprotein contained in the present molecular weight marker is a glycoprotein comprising a peptide chain bound to a sugar chain, as described above and, thus, is a branched polymer. On the other hand, molecular weight markers conventionally used are synthetic polymers and are only linear polymers without branches. Therefore, the present molecular weight markers can more accurately determine the molecular weights of branched polymers (e.g., glycoproteins), which have been difficult to accurately determine using the synthetic linear polymers provided as conventional molecular weight markers, since linear polymers are different from branched polymers in hydrodynamic radiuses or shapes.

Hereinafter, the present invention will be described in more detail with reference to Examples. However, the technical scope of the present invention is not intended to be limited to these Examples.

EXAMPLE 1

Figure 2:
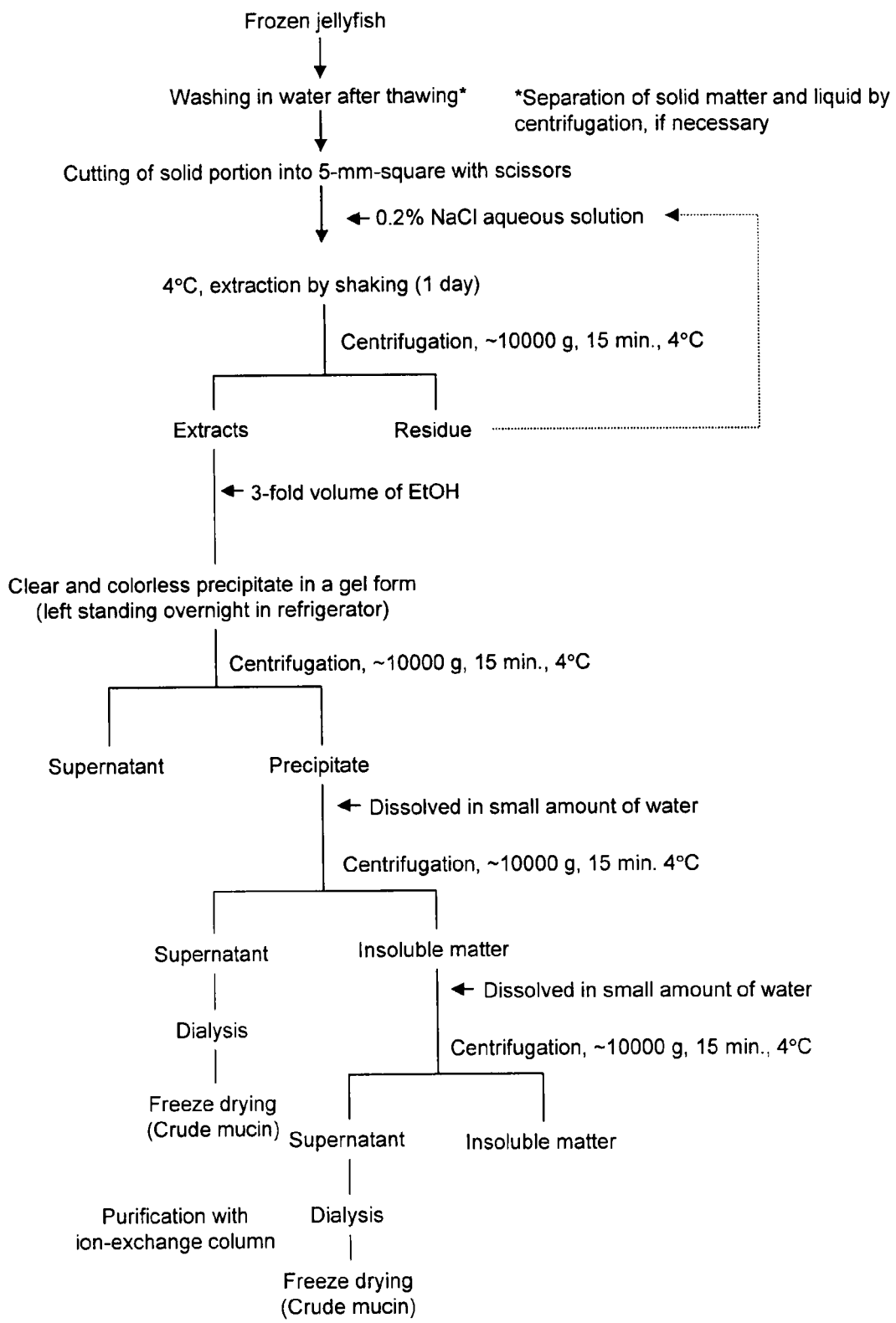
FIG. 2 shows the specific procedures for isolating a mucin-type glycoprotein.

Crude mucin serving as a precursor of a novel mucin-type glycoprotein according to the present invention was extracted from moon jelly (*Aurelia aurita*) and brown jellyfish (*Chrysaora melanaster*) by the following method, as shown in FIG. 2:
1) A whole jellyfish in a frozen state was thawed and then washed in water, and solid matter and liquid were separated by centrifugation;
2) The remaining solid portion was cut into fragments of approximately 5 mm to 1 cm square with scissors;
3) The fragments were subjected to degreasing and dehydration by acetone treatment and then swollen with water;
4) The solid sample was added to a 0.2% NaCl aqueous solution and subjected to extraction by shaking at 4° C.;
5) The solution from step 4 was centrifuged at 4° C. at 10000 g for 15 minutes;
6) To the extracts from step 5, 3-fold volume of ethanol was added to give precipitates in a gel form;
7) The solution from step 6 was left standing overnight in a refrigerator and then centrifuged at 4° C. at 10000 g for 15 minutes;
8) The precipitates from step 7 were dissolved in a small amount of water, and the solution was centrifuged at 4° C. at 10000 g for 15 minutes;
9) The supernatant from step 8 was removed and purified by dialysis, and freeze-dried to prepare crude mucin; and
10) the precipitates from step 8 were further subjected to the steps 7 and 8 repeated appropriate times to obtain crude mucin.

EXAMPLE 2

Figure 3:
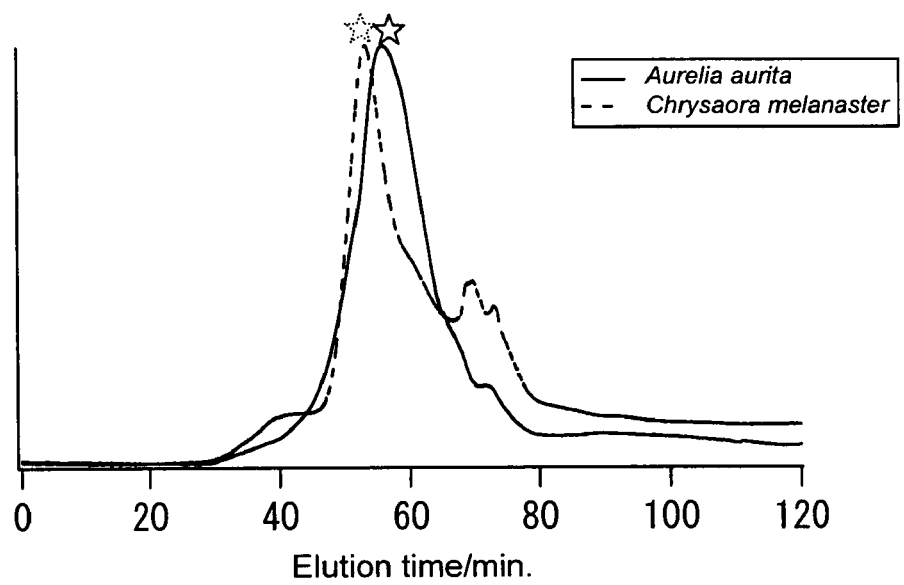
FIG. 3 shows the result of subjecting crude mucins from moon jelly (*Aurelia aurita*; solid line) and brown jellyfish (*Chrysaora melanaster*; dotted line) to ion-exchange liquid chromatography. The asterisks denote peaks of the mucin-type glycoprotein.

The crude mucins from two jellyfishes obtained in Example 1 were subjected to ion-exchange liquid chromatography, and peaks with asterisks shown in FIG. 3 were purified to thereby obtain mucin-type glycoproteins with high purity.
Conditions for chromatography used are as follows:
TSK gel DEAE-ToyoPearl 650M 25 mm i.d.×150 mm
A: 10 mMNaPi, pH 7
B: 0.5 M NaCl/10 mM NaPi, pH 7
flow 2 ml/min, detector UV (215 nm)
gradient 0-60 min (% B: 0-100)
sample: Moon jelly (*Aurelia aurita*)
5 ml (2 mg/ml crude mucin/10 mM NaPi solution)
Brown jellyfish (*Chrysaora melanaster*)
1.3 ml

EXAMPLE 3

The compounds purified in Example 2 were subjected to constituent amino acid analysis using an automatic amino acid analyzer. Each of the samples (approximately 12 μg each) purified by ion-exchange chromatography and dialyzed as described above was transferred to a hydrolysis tube and evaporated to dryness with a centrifuge evaporator. The dried sample was placed in an outer tube containing constant boiling hydrochloric acid (5.7 N) and sealed under reduced pressure. Hydrolysis was performed at 110° C. for 20 hours by a gas phase method.

The outer tube was opened, and the hydrolysis tube was subjected to drying in the same way. The dried hydrolysate was dissolved in 100 μl of 0.02 N hydrochloric acid. A high-speed amino acid analyzer L-8500A (manufactured by Hitachi Ltd.) was used in the amino acid analysis of the hydrolysate. The amino acids in the hydrolysate were separated with five buffer solutions using an ion-exchange column according to the special amino acid analysis method specified by the manufacture (Hitachi Ltd.) The separated amino acids were reacted with ninhydrin by a post-column method and detected with visible lights at two wavelengths. Based on values obtained by analyzing 2 nmol of a standard amino acid mixture, glucosamine, and galactosamine, aminosugars and normal amino acids were quantified using a chromatogram at 570 nm, while proline was quantified using a chromatogram at 440 nm n.

The results of amino acid composition analysis are shown in FIG. 4. As shown in the amino acid concentration ratio in FIG. 4, the composition of the peptide portion in the mucin-type glycoprotein was demonstrated to be threonine (Thr): glutamic acid (Glu):proline (Pro):alanine (Ala):valine (Val)+ isoleucine (Ile):N-acetylgalactosamine (GalNAc) of 2:1:1:2: 2:2 within 10% error each in both moon jelly (*Aurelia aurita*) and brown jellyfish (*Chrysaora melanaster*). Moreover, the concentration ratio of serine or other amino acids was as small as approximately 0.05%. Therefore, these were probably derived from impurities or the terminal structures and were considered to have no relation to the repeat structure of the mucin-type glycoprotein.

EXAMPLE 4

In the present Example, the proteins (1.8 μg each) purified in Example 2 were analyzed by a pulse liquid phase method using Applied Biosystems Procise 494 HT to plot a PTH amino acid amount in each cycle.

Figures 1, 5:
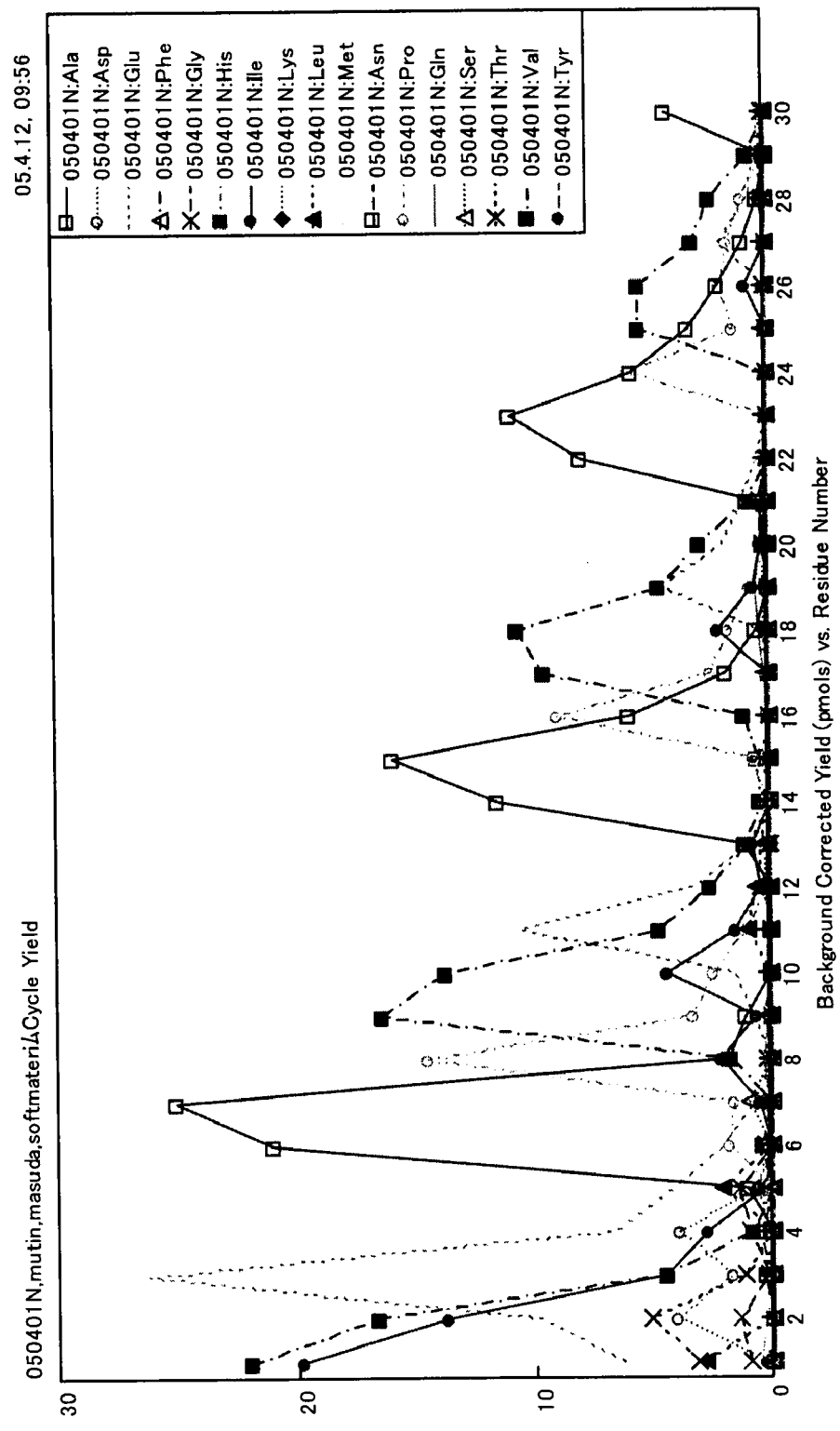
Figures 2, 5:
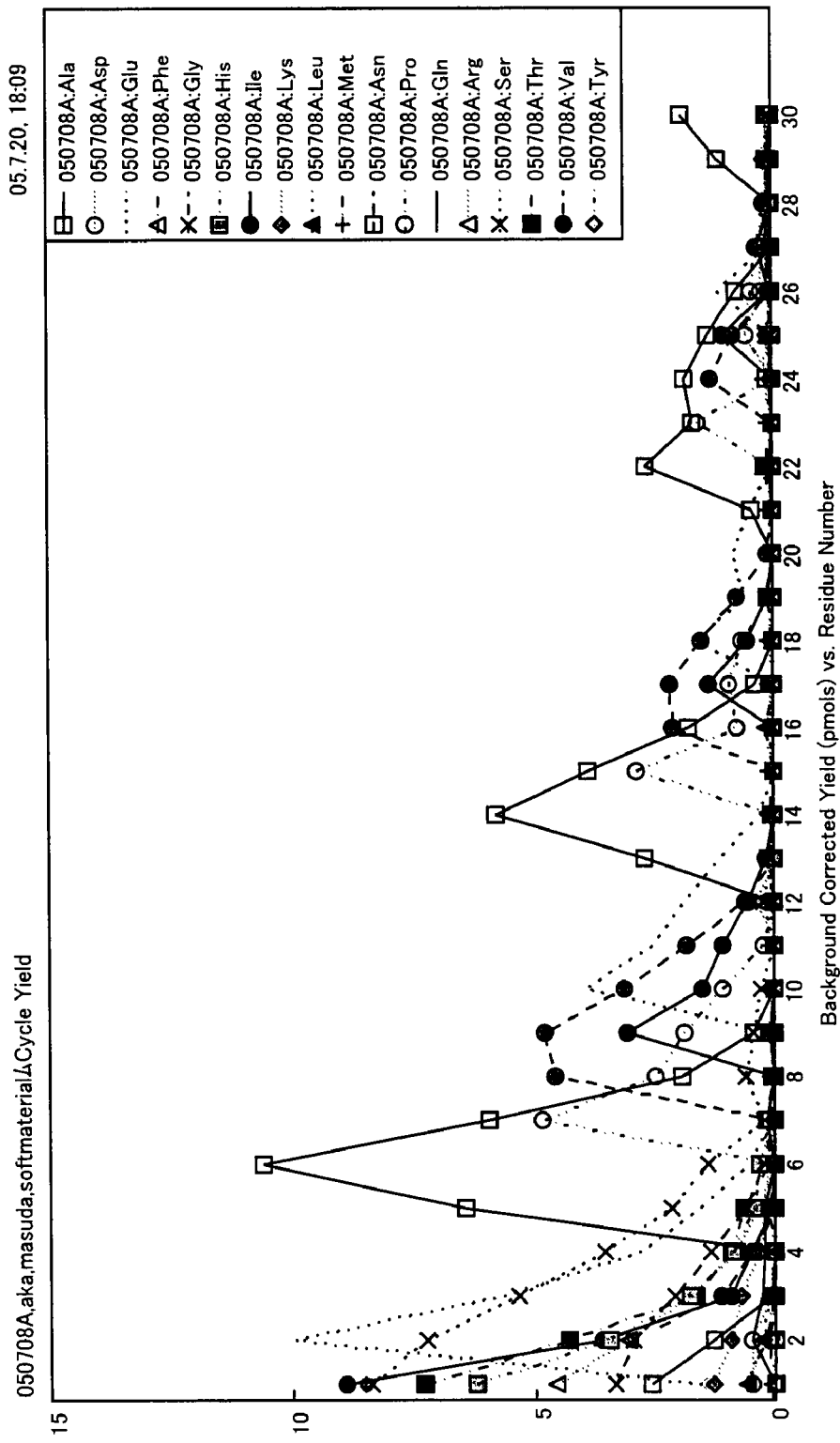

The amino acid sequence analysis results of the mucin-type glycoproteins obtained from two jellyfishes from the amino termini are shown in FIG. 5 (FIG. 5-1 shows the results from *Aurelia aurita*, and FIG. 5-2 shows the results from *Chrysaora melanaster*). In FIG. 5-1, the alternate long and short dashed line with filled squares denotes valine (Val); the dashed line denotes glutamic acid (Glu); the line with open squares denotes alanine (Ala); the chain double-dashed line with open circles denotes proline (Pro); and the line with filled circles denotes isoleucine (Ile). Thirty residues were analyzed with an automatic protein amino acid sequence analyzer. As a result, 3.75 cycles of a repeat structure comprising, from the N-terminus, Val-Val (Ile)-Glu-X-X-Ala-Ala-Pro (X represents an unknown amino acid) (SEQ ID NO: 5) was identified. This demonstrated that the mucin-type glycoprotein comprises the repeating sequences of VVEXX-AAP (SEQ ID NO: 6) (in some cases, VIEXXAAP (SEQ ID NO: 7)). Moreover, from the results of Example 3, X was expected to be threonine. This mucin having the repeating amino acid sequences comprising eight residues is a protein that cannot be found by search in Protein Data Bank and so on and has not been discovered so far. Thus, it is concluded that this protein is novel.

Moreover, the obtained mucin-type glycoprotein corresponds to 60 μmol, provided that the early yield is approximately 30 μmol and the early yield in Edman degradation is 50%. Thus, the number of the repeating units (the molecular weight of the peptide portion: approximately 768, the molecular weight including a sugar chain described later: approximately 1500) was also found to be approximately 40.

The molecular weight 60 kDa determined by this value may be regarded as a number-average molecular weight.

The repeating units of VEXXAAPV (SEQ ID NO: 3) (in some cases, IEXXAAPV (SEQ ID NO: 8)) from the N-terminus were obtained from brown jellyfish (*Chrysaora melanaster*) (FIG. 5-2). This was the same as the repeating units from moon jelly (*Aurelia aurita*) except that the first residue was absent. Basically, these repeating units did not differ from each other by any means.

EXAMPLE 5

Each of the samples (approximately 6 μg) purified by ion-exchange chromatography and dialyzed as described above was transferred to a reaction tube and evaporated to dryness with a centrifuge evaporator. The sialic acid contained therein was converted to free, reducing sugars by the addition of an enzyme and then hydrolyzed at 100° C. for 3 hours using trifluoroacetic acid (4 M). After N-acetylation, the sample was fluorescently labeled (ABEE) and then separated with a mixed solvent of 0.2 M potassium borate buffer solution (pH 8.9)/acetonitrile (93:7) using a Honen Pak C18 column (75 mm×4.6 mm i.d.). Detection was conducted using fluorescence at 305 μm. A monosaccharide composition ratio was quantified based on the chromatogram of a standard mixture of 11 monosaccharides treated in the same way.

Figures 1, 6:
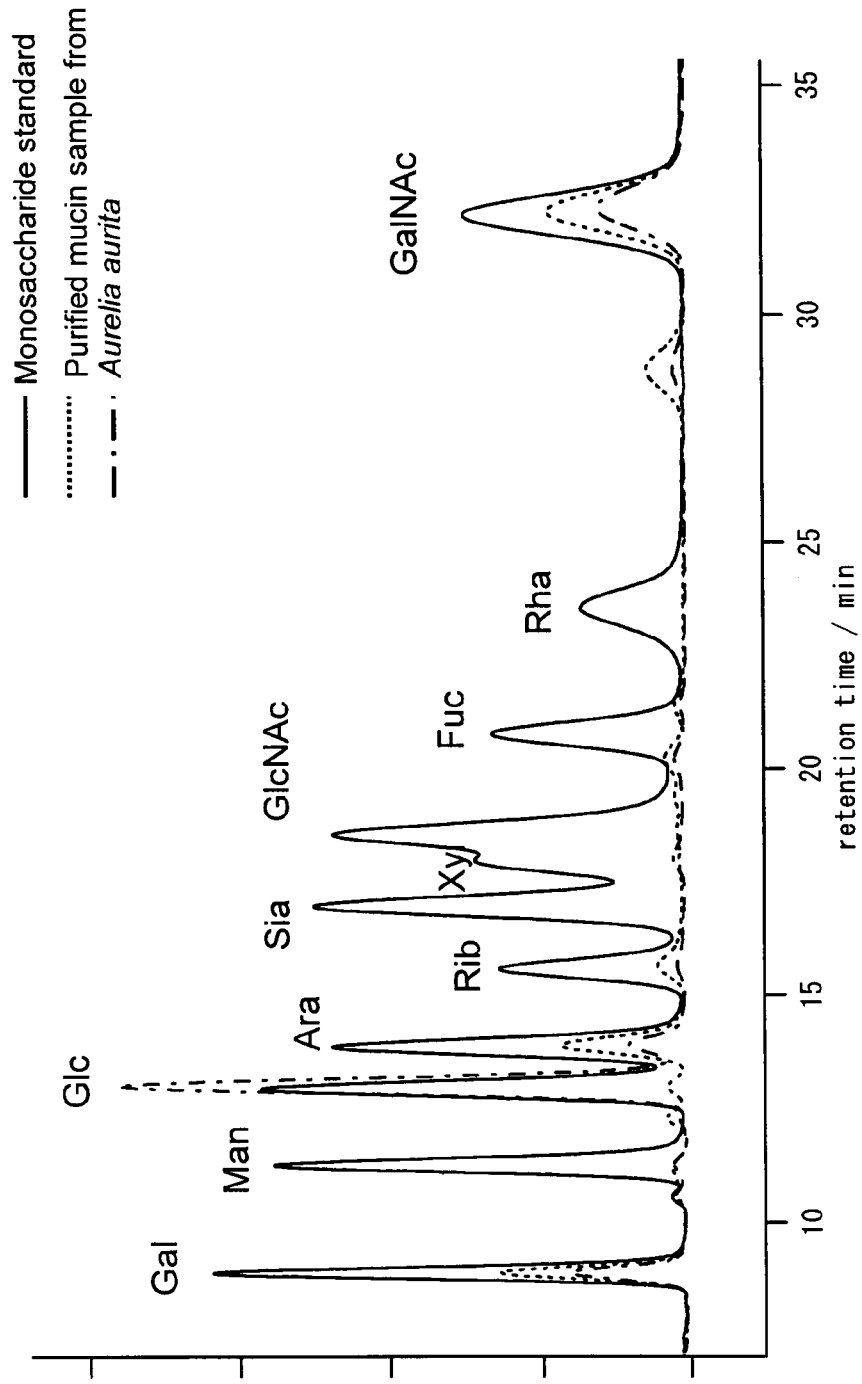
Figures 2, 6:
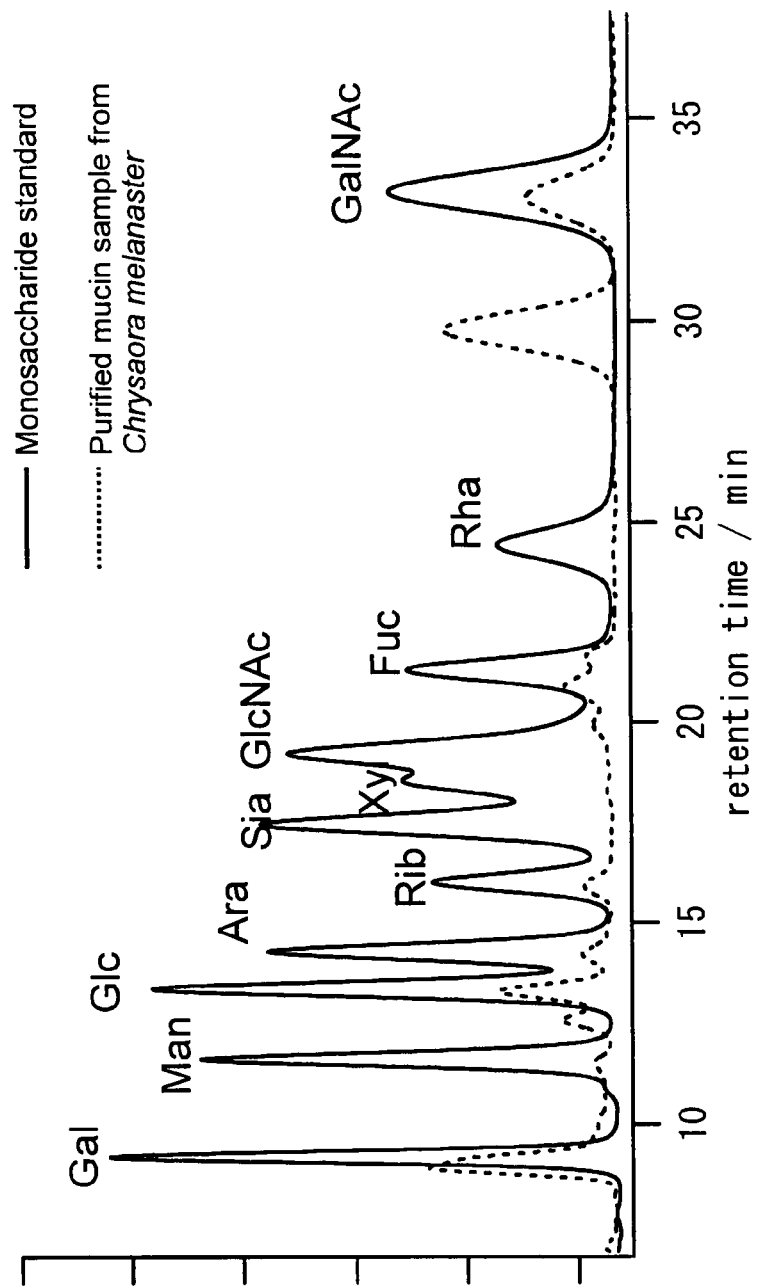

FIG. 6-1 shows the results from *Aurelia aurita*, and FIG. 6-2 shows the results from *Chrysaora melanaster*.

The propositions of monosaccharides estimated from the monosaccharide composition analysis of the present mucin-type glycoprotein from *Aurelia aurita* shown in FIG. 6-1 are as follows:

|  | (Alternate long and short dashed line) | (Dashed line) |
|---|---|---|
| Galactose | 0.6 nmol | 0.9 nmol |
| N-acetylgalactosamine | 0.8 nmol | 1.2 nmol |

These results of the analyses suggest that two threonines in the repeating units of the peptide are each bound to N-acetyl-galactosamines, all or some of which are in turn bound to galactose. Assuming that other sugars are not bound therewith, the sugar chain portion has a molecular weight of 730. Thus, the estimated molecular weight of the unit glycoprotein is approximately 1500 (sugar content: approximately 50%).

On the other hand, the monosaccharide composition analysis of the present mucin-type glycoprotein from *Chrysaora melanaster* shown in FIG. 6-2 had no standard samples and involved unidentifiable unknown sugars. Therefore, the proportion of monosaccharide to all of the sugars was unknown. The concentrations of known monosaccharides estimated from the present analysis are as follows:

|  | (Dashed line) |
|---|---|
| Galactose | 0.7 nmol |
| N-acetylgalactosamine | 0.8 nmol |

EXAMPLE 6

A part of the sample of 0.05 ml (1 mg/ml purified novel mucin/0.1 M NaPi solution) was used to perform a gel filtration (size exclusion) HPLC analysis on the present mucin-type glycoprotein from *Aurelia aurita* in Shodex SB-806HQ, eluent: 0.1 M NaPi, pH 7, flow: 0.5 ml/min, detector UV (215 nm) & RI. Pullulan was used as a molecular weight marker.

Figure 7:
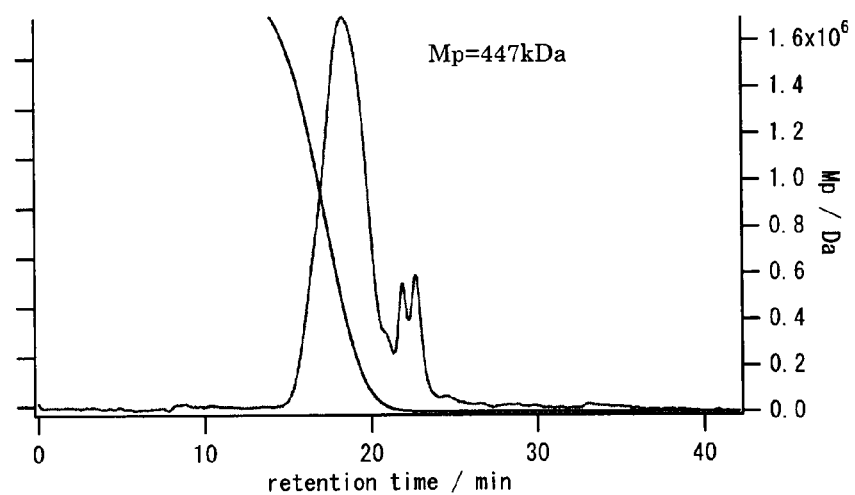
FIG. 7 shows the result of a gel filtration (size exclusion) HPLC analysis of a purified mucin-type glycoprotein from moon jelly (*Aurelia aurita*)
Figure 7:
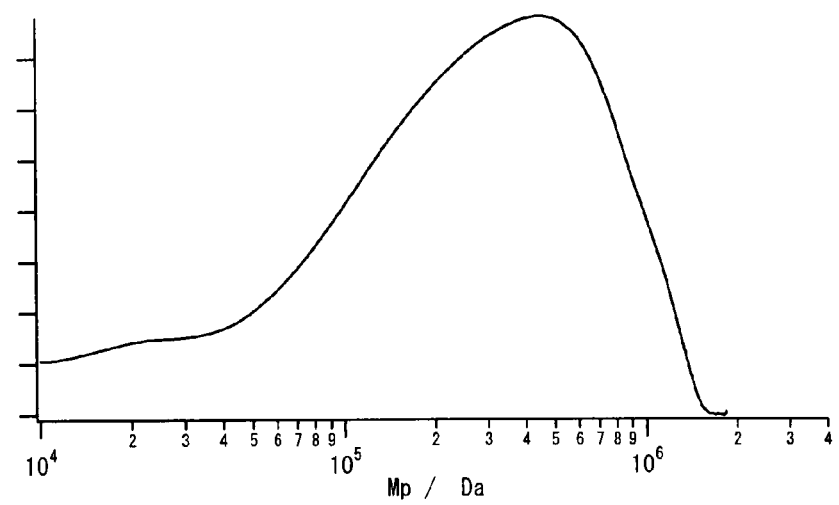

The results of the analysis are shown in FIG. 7. The results showed that the peak molecular weight was approximately 450 kDa (FIG. 7A). Moreover, number-average and weight-average molecular weights calculated from the chromatogram are approximately 180 kDa and approximately 500 kDa, respectively (FIG. 7B). The molecular weight distribution was shown to be 10 to 1400 kDa in gel filtration using pullulan as a standard substance.

The number-average molecular weight determined by gel filtration was approximately 180 kDa, which differed by 3 times from the molecular weight 60 kDa estimated from amino acid sequence analysis. Two most reliable measurement methods are currently used as the molecular weight measurement of polymer sugar chain compounds. However, these two methods may lead to errors such that the absolute value may vary by several times. Such errors are regarded as falling within a usually possible range under current techniques and thought to be inescapable in the molecular weight measurement of polymer sugar chain compounds. Considering the problem of compatibility of the standard substance (pullulan) used in relative measurement, the absolute value of the number-average molecular weight seems to be more accurate for that based on the number of the repeating units obtained from amino acid sequence analysis than that from gel filtration. Specifically, under present circumstances, the amino acid sequence analysis can determine the absolute value of an accurate molecular weight but cannot determine molecular weight distribution, whereas the gel filtration method can determine only molecular weight distribution, which is just a relative value. This could be confirmed actually by procedures below including Examples 7 to 9.

The molecular weight distribution determined by gel filtration was converted to an absolute value by a method using MALDI-TOF shown in Example 9. In the present specification, this approach is used as a reference measurement method for defining molecular weights. The value of the molecular weight determined by MALDI-TOF was in good agreement with the molecular weight estimated from amino acid sequence analysis. The ratio between the number-average molecular weights ((the molecular weight based on pullulan as a standard)/(the molecular weight determined by MALDI-TOF)=approximately 3) determined by these two methods held in all cases of the molecular weights. After correction by this value, the peak molecular weight is 150 kDa; the weight-average molecular weight is 170 kDa; and the upper limit of the peak molecular weight obtained by the chromatography is 470 kDa. The number of the repeating amino acid sequences corresponding thereto is 100 for the peak value, 110 for the weight-average molecular weight, and 700 for the upper limit of the molecular weight.

Moreover, the chromatogram shows that 50% of the total is included in the range of 60 to 270 kDa (after correction) with the peak molecular weight of 150 kDa and that 30% of the total is included in the range of 90 to 210 kDa (after correction). That is, it was demonstrated that 50% of the total has 40 to 180 repeating units, and that 30% of the total has 60 to 150 repeating units.

EXAMPLE 7

In the present Example, mucin-type glycoproteins extracted from a variety of jellyfishes were subjected to size exclusion chromatography (SEC).

Figure 8:
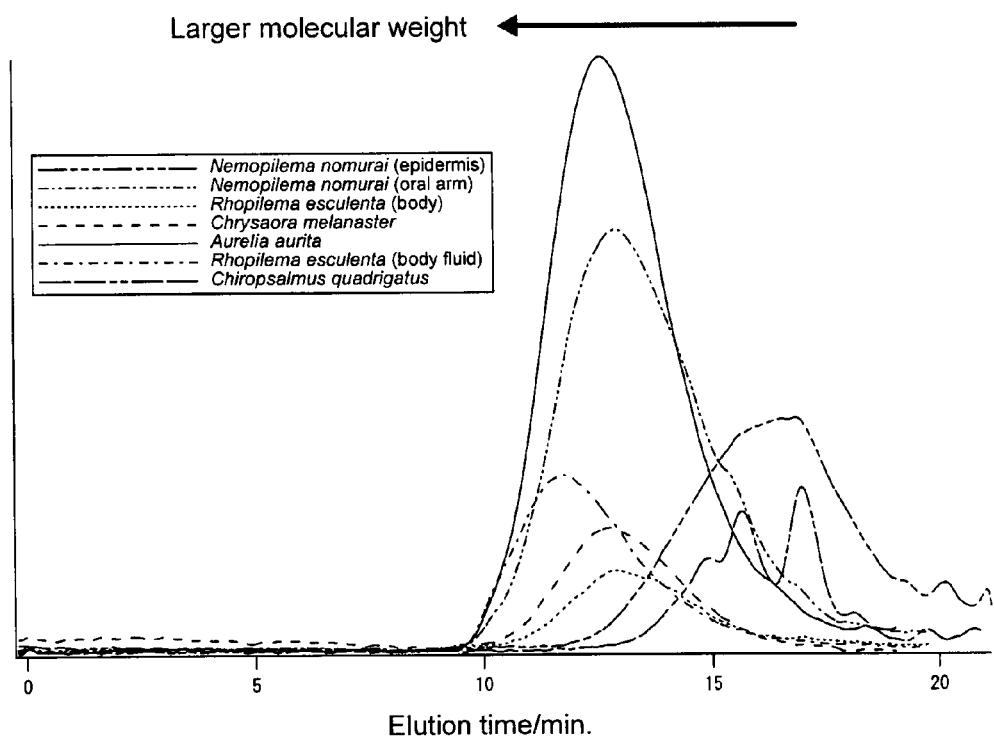
FIG. 8 shows the results of size exclusion chromatography analyses of mucin-type glycoproteins from a variety of jellyfishes or parts thereof.

The mucin-type glycoprotein extraction from jellyfishes was performed in the same way as in Example 1. Conditions for chromatography are as follows:

Column: TSK gel G5000PW$_{XL}$
Eluent: 0.1 M ammonium acetate aqueous solution
Flow rate: 0.5 ml/min.
Sample concentration: 0.3 to 0.9 mg/ml The results are shown in FIG. 8. The results of FIG. 8 demonstrated that the mucin-type glycoproteins from jellyfishes have wide molecular weight distribution. Particularly, the mucin-type glycoprotein obtained from the umbrella surface (epidermis) of Echizen-kurage jellyfish (*Nemopilema nomurai*) exhibited a lower molecular weight and a wider range of molecular weight distribution than those from other species.

EXAMPLE 8

Figure 9:
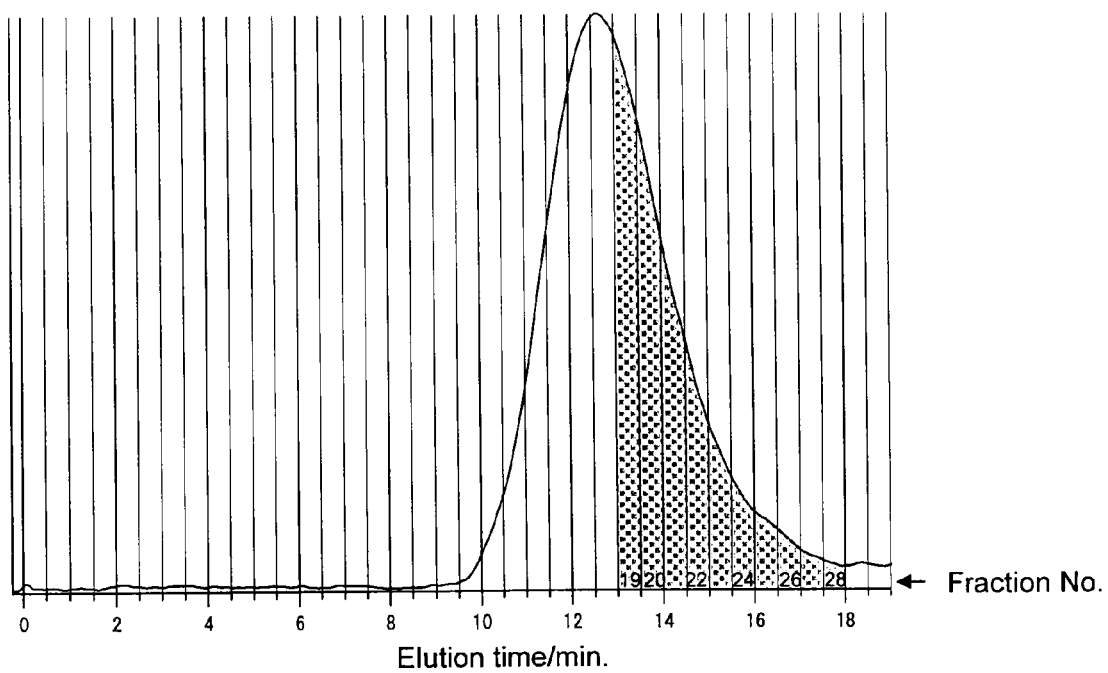
FIG. 9 shows the fractions obtained by subjecting a mucin-type glycoprotein from moon jelly (*Aurelia aurita*) to size exclusion chromatography, followed by fractionation.

The mucin-type glycoprotein from Aurelia aurita subjected to SEC in Example 7 was fractionated into each fraction shown in FIG. 9 and subjected to MALDI-TOF mass spectrometry. The MALDI-TOF MS was conducted using the apparatus Reflex manufactured by Bruker Daltonics in linear mode using trans-indole-3-acrylic acid as a matrix.

Figure 10:
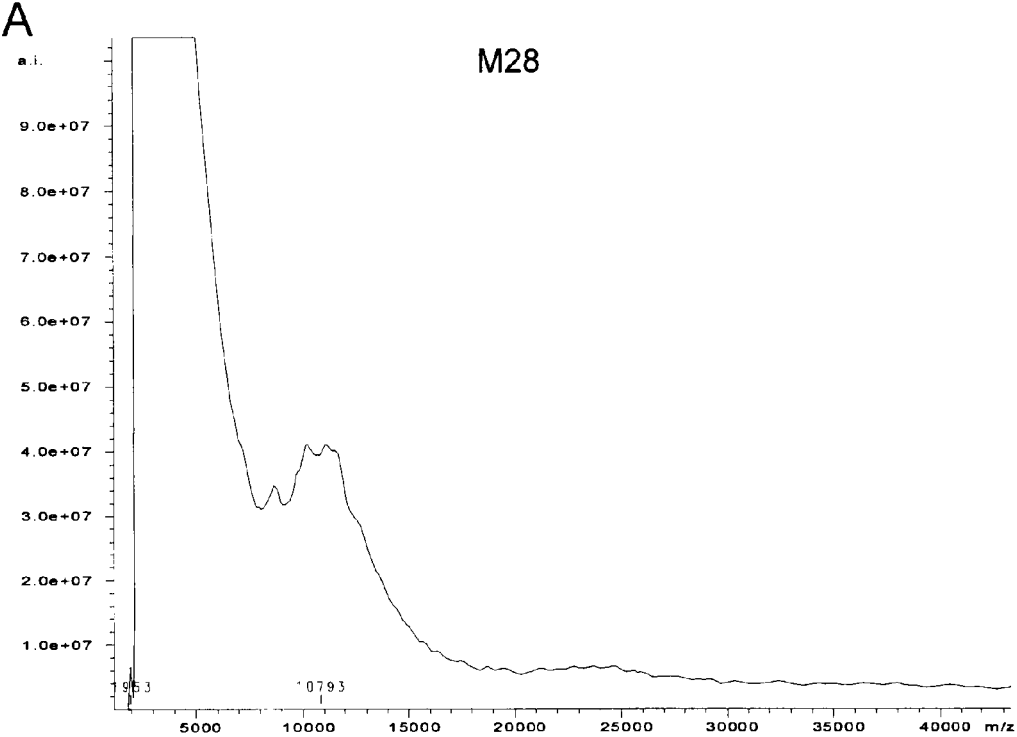
Figure 1:
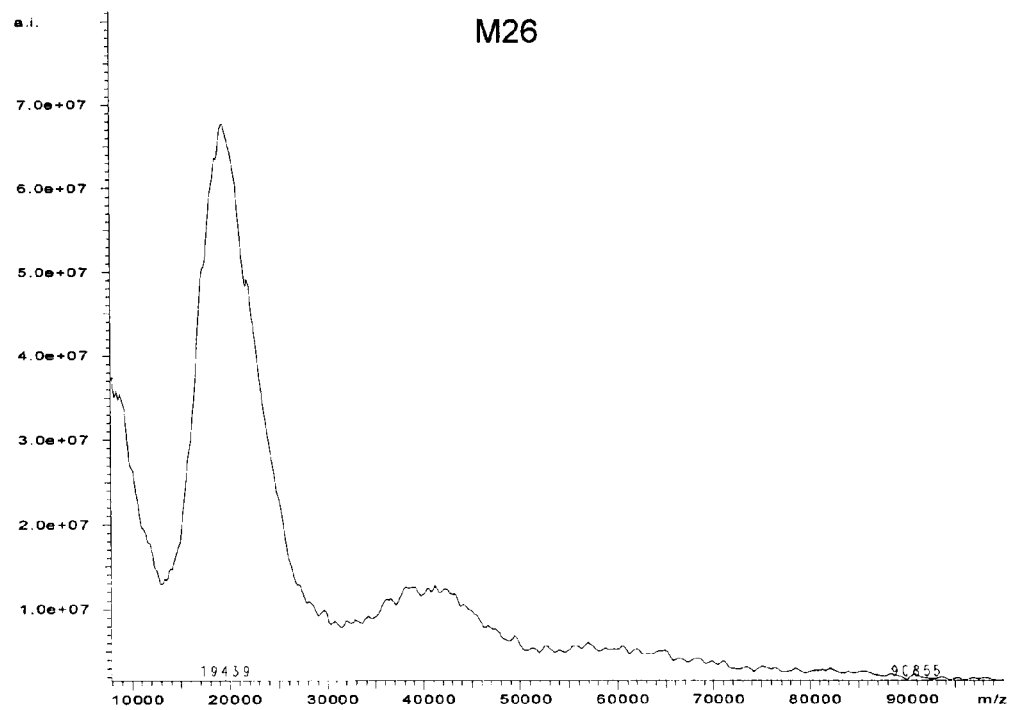
Figure 10:
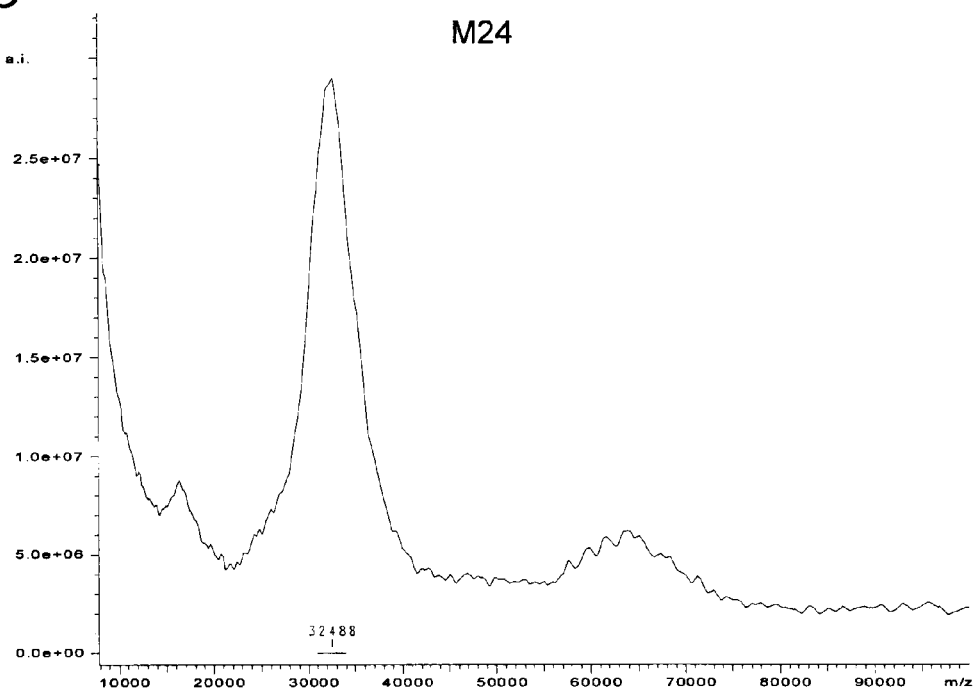
Figure 2:
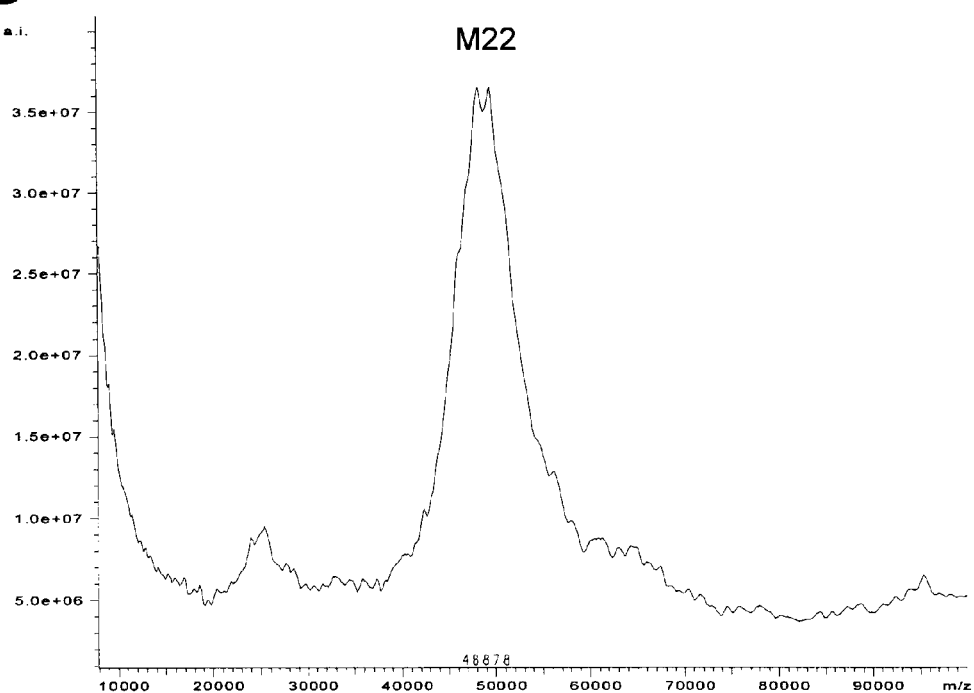
Figure 10:
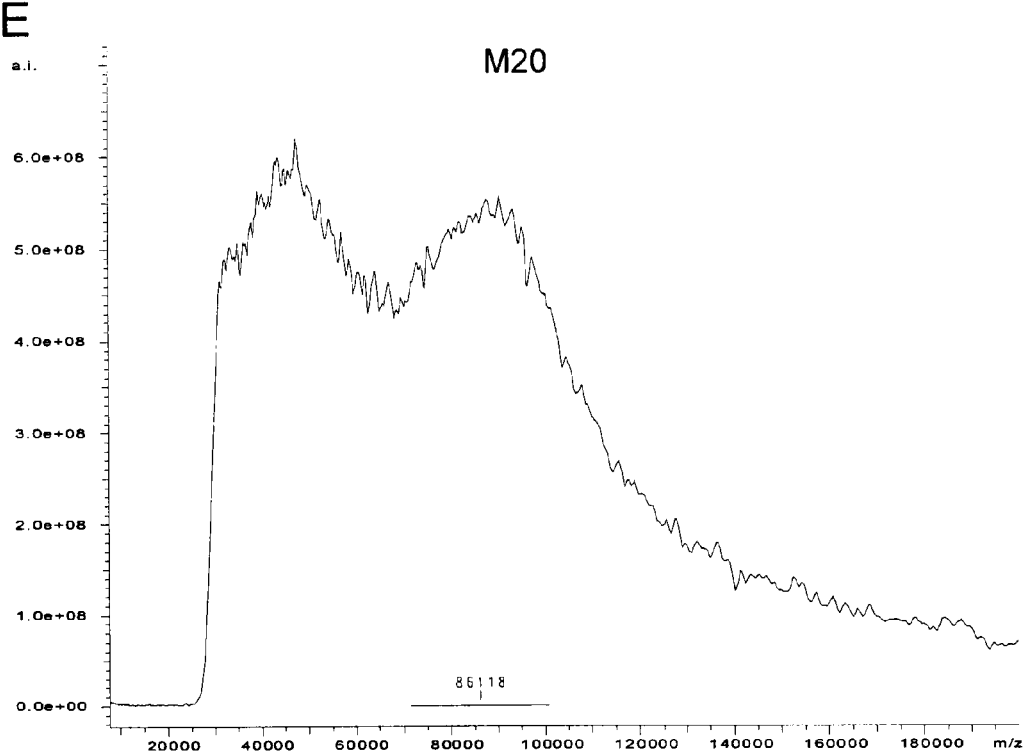
Figure 3:
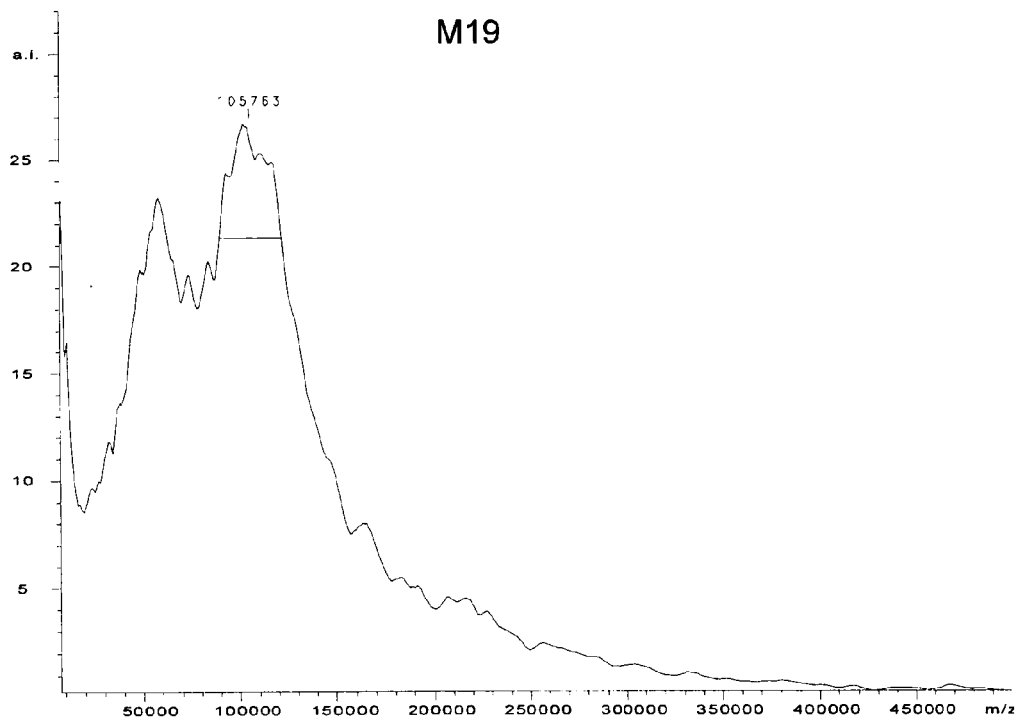

The results are shown in FIG. 10. In the diagram, M+two-digit number described in the title portion denotes the fraction numbers in FIG. 9. Since a clear peak was obtained in each fraction, molecular weights can be determined based thereon. Specifically, in FIG. 10, according to calculation by visual observation, the molecular weight distribution (and its median) was approximately 8 to 15 kDa (median: 11 kDa) for M28 fraction; approximately 15 to 25 kDa (median: 19 kDa) for M26 fraction; approximately 28 to 38 kDa (median: 32 kDa) for M24 fraction; approximately 45 to 55 kDa (median: 49 kDa) for M22 fraction; approximately 70 to 100 kDa (median: 86 kDa) for M20 fraction; and approximately 80 to 150 kDa (median: approximately 110 kDa) for M19 fraction.

EXAMPLE 9

The mucin-type glycoprotein from *Aurelia aurita* subjected to SEC in Example 7 was fractionated into each fraction shown in FIG. 9. The molecular weights measured in MALDI-TOF MS in Example 8 were plotted. The results of a measurement of pullulan were also plotted as a control.

Figure 11:
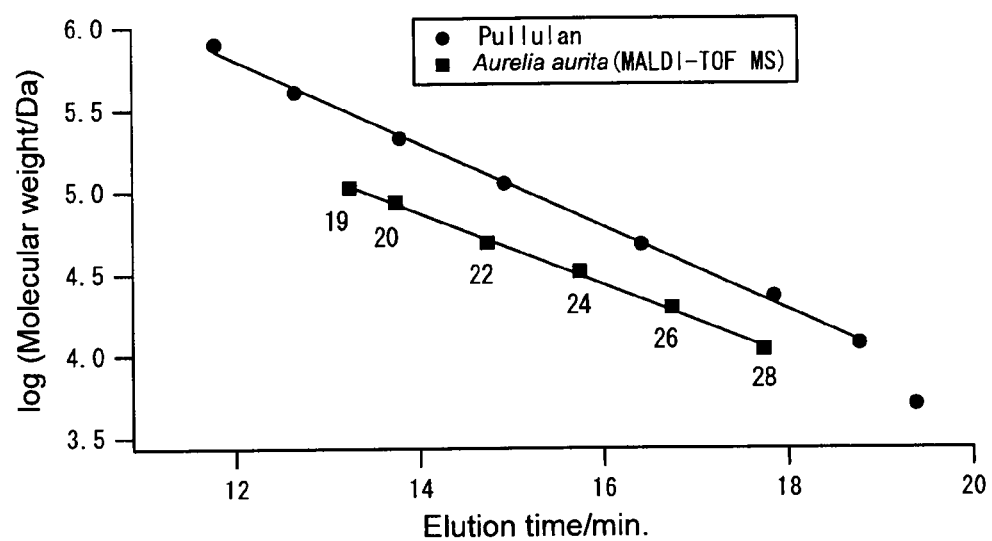
FIG. 11 is the graph plotting the molecular weights of a mucin-type glycoprotein from moon jelly (*Aurelia aurita*) and pullulan.

The results are shown in FIG. 11. In FIG. 11, the numbers shown below the results of the mucin-type glycoprotein (filled squares) denote fraction numbers in FIG. 9. These results demonstrate that both the mucin-type glycoprotein from jellyfish and pullulan give a good linear relationship, while the absolute values thereof differ by approximately three times. Thus, it was shown that the present mucin-type glycoprotein can be used as a molecular weight marker, particularly for the molecular weight measurement of polymer compounds such as glycoproteins, by fractionation as described above.

EXAMPLE 10

The mucin-type glycoprotein of the present invention was examined for its hygroscopic and moisturizing properties. The hygroscopic properties were measured as follows: the purified mucin-type glycoprotein from moon jelly (*Aurelia aurita*) was dried to a constant weight in a desiccator containing silica gel, and a 20 mg aliquot thereof was collected into a weighing bottle and left in a desiccator adjusted to a relative humidity (RH) of approximately 79% (25° C.) with a saturated aqueous solution of ammonium sulfate. The weight gain of this sample was measured over time, and the amount of the weight gain was shown as the amount of water absorbed. The results are shown in Table 1 below.

On the other hand, the moisturizing properties were measured in a similar way as follows: the purified mucin-type glycoprotein from moon jelly (*Aurelia aurita*) was dried to a constant weight in a desiccator containing silica gel, and a 20 mg aliquot thereof was collected into a weighing bottle and, after the addition of 10% of water, left in a desiccator adjusted to RH of approximately 49% with a saturated aqueous solution of sodium hydroxide. The weight loss of this sample was measured after 24 hours, and the amount of water retained was calculated. The results are also shown in Table 1 below.

These two measured values were determined as relative values using hyaluronic acid as a standard substance, which has high moisturizing and hygroscopic properties and has been used as a moisturizing component in cosmetic materials.

TABLE 1

|  | Hygroscopic properties (RH 79%) | | | Moisturizing properties |
| --- | --- | --- | --- | --- |
|  | After 6 hours | After 19.5 hours | After 24 hours | (RH 49%) After 24 hours |
| Hyaluronic acid | 1.0 | 1.0 | 1.0 | 1.0 |
| Mucin-type glycoprotein | 3.0 | 3.0 | 3.0 | 0.6 |

* The values are indicated as relative values to the values for hyaluronic acid with a nominal molecular weight of 300 kDa defined as 1.0.

These results show, as to hygroscopic properties, that the purified mucin-type glycoprotein of the present invention exhibits approximately three times the hygroscopic properties of hyaluronic acid and is excellent in short-time hygroscopic properties.

These results also show, as to moisturizing properties, that the purified mucin-type glycoprotein of the present invention exhibits approximately 60% of the moisturizing properties of hyaluronic acid, which has exceedingly high moisturizing properties, in a low-humidity condition of relative humidity (RH) of 49% or lower.

All publications, patents, and patent applications cited in this specification are incorporated herein by reference in their entirety.

INDUSTRIAL APPLICABILITY

The present invention provides a novel mucin-type glycoprotein. The mucin-type glycoprotein can be used as, for example, a substitute substance for human mucin having an accurately identified chemical structure and is useful in fields such as pharmaceutical, agricultural, and food fields. Moreover, the mucin-type glycoprotein is produced easily in large amounts from jellyfishes and is therefore excellent from economical and environmental standpoints.

Moreover, the present invention provides molecular weight markers comprising mucin-type glycoproteins. The molecular weight markers have branched polymer chains obtained from natural polymers. The use of the present molecular weight markers allow for the accurate determination of the molecular weights of branched polymers such as glycoproteins.

The invention claimed is:

1. An isolated mucin-type glycoprotein having a repeat structure which comprises 3 to 2000 repeating units, wherein each repeating unit is the amino acid sequence of Val-Xaa-Glu-Thr-Thr-Ala-Ala-Pro (SEQ ID NO: 1), wherein Xaa is Val or Ile, and one or more amino acid residues in said isolated mucin-type glycoprotein is glycosylated with a sugar chain consisting of one or more monosaccharides.

2. The isolated mucin-type glycoprotein according to claim 1, wherein the repeat structure comprises 3 to 700 repeating units.

3. The isolated mucin-type glycoprotein according to claim 1, wherein the repeat structure comprises 40 to 180 repeating units.

4. The isolated mucin-type glycoprotein according to claim 1, wherein the amino acid residue glycosylated with a sugar chain is threonine (Thr).

5. The isolated mucin-type glycoprotein according to claim 4, wherein 98% or more of the amino acid residues glycosylated with a sugar chain are threonine (Thr).

6. The isolated mucin-type glycoprotein according to claim 1, wherein the sugar chain comprises a monosaccharide selected from the group consisting of N-acetylgalactosamine, galactose, N-acetylglucosamine, sialic acid, arabinose, and fucose.

7. The isolated mucin-type glycoprotein according to claim 6, wherein the sugar chain comprises N-acetylgalactosamine.

8. The isolated mucin-type glycoprotein according to claim 6, wherein the sugar chain comprises N-acetylgalactosamine and galactose.

9. The isolated mucin-type glycoprotein according to claim 1, wherein the mucin-type glycoprotein is extracted from a jellyfish.

10. The isolated mucin-type glycoprotein according to claim 1 produced by a method comprising the steps of: (a) cutting the solid portions of a jellyfish; (b) preparing an extract of the cuttings of the solid portions of the jellyfish with a salt solution; (c) separating the mucin-type glycoprotein according to claim 1 from the extract by centrifugation and dialysis; and purifying the mucin-type glycoprotein according to claim 1.

11. The isolated mucin-type glycoprotein according to claim 1, wherein the isolated mucin-type glycoprotein is freeze-dried.

12. A method for producing the mucin-type glycoprotein according to claim 1 comprising the steps of: (a) cutting the solid portions of a jellyfish; (b) preparing an extract of the cuttings of the solid portions of the jellyfish with a salt solution; (c) separating the mucin-type glycoprotein according to claim 1 from the extract by centrifugation and dialysis; and purifying the mucin-type glycoprotein according to claim 1, wherein all of the steps are performed at 0 to 25° C.

13. A composition comprising the isolated mucin-type glycoprotein according to claim 1.

14. The composition according to claim 13, wherein the composition is in the form of an aqueous solution or resin.

15. A method for modifying the sugar chain of the mucin-type glycoprotein according to claim 1, comprising contacting the isolated mucin-type glycoprotein according to claim 1 with a glycosyltransferase to thereby modify the sugar chain of the isolated mucin-type glycoprotein according to claim 1.

16. A method for measuring molecular weights of the isolated mucin-type glycoprotein according to claim 1 comprising the steps of: (a) subjecting the mucin-type glycoprotein according to claim 1 to size exclusion chromatography for fractionation; (b) collecting and purifying the mucin-type glycoprotein from the fractionation; and (c) measuring molecular weights of the purified mucin-type glycoprotein.

17. The method according to claim 16, the method further comprising the step of: (d) freeze-drying the purified mucin-type glycoprotein.

* * * * *